United States Patent [19]
Ausubel et al.

[11] Patent Number: 6,004,783
[45] Date of Patent: Dec. 21, 1999

[54] CLEAVED AMPLIFIED RFLP DETECTION METHODS

[75] Inventors: Frederick Ausubel, Newton, Mass.; Ronald W. Davis, Palo Alto; Daphne Preuss, Foster City, both of Calif.

[73] Assignee: The General Hospital Corporation, Boston, Mass.

[21] Appl. No.: 08/715,484

[22] Filed: Sep. 18, 1996

Related U.S. Application Data

[63] Continuation-in-part of application No. 08/210,226, Mar. 18, 1994, abandoned, and application No. PCT/US95/03419, Mar. 17, 1995.

[51] Int. Cl.$^6$ .............................. C12Q 1/68; C07H 21/02; C07H 21/04
[52] U.S. Cl. ........................... 435/91.2; 435/6; 536/23.1; 536/24.3; 536/24.33
[58] Field of Search .................................. 435/4, 6, 91.2; 536/23.1, 24.3, 24.33

[56] References Cited

U.S. PATENT DOCUMENTS

| | | | |
|---|---|---|---|
| 4,683,194 | 7/1987 | Saiki et al. | 435/6 |
| 4,683,202 | 7/1987 | Mullis | 435/91 |
| 4,775,619 | 10/1988 | Urdea | 435/6 |
| 4,925,785 | 5/1990 | Wang et al. | 435/6 |
| 5,118,605 | 6/1992 | Urdea . | |
| 5,192,659 | 3/1993 | Simons | 435/6 |
| 5,200,314 | 4/1993 | Urdea | 435/6 |
| 5,294,534 | 3/1994 | Dattagupta et al. | 435/6 |
| 5,523,225 | 6/1996 | Kraus | 435/240.1 |
| 5,629,158 | 5/1997 | UHlen et al. | 435/6 |

FOREIGN PATENT DOCUMENTS

| | | |
|---|---|---|
| 0 327 429 | 8/1989 | European Pat. Off. . |
| WO90/06670 | 6/1990 | WIPO . |

OTHER PUBLICATIONS

Guo et al., Nucleic Acids Research 22:5456–5465 (1994).
Lisitsyn et al., Science 259:946–951 (1993).
Cox and Lehrach, "Genome Mapping: PCR Based Meiotic and Somatic Cell Hybrid Analysis," BioEssays 13:193–198 (1991).
Konieczny and Ausubel, "A Procedure for Mapping Arabidopsis Mutations Using Co–dominant Ecotype–specific PCR–based Markers," The Plant Journal 4:403–410 (1993).
Kostyu et al., "Rapid HLA–DR Oligotyping by an Enzyme–Linked Immunosorbent Assay Performed in Microtiter Trays," Human Immunology 38:148–158 (1993).
Mullis and Faloona, "Specific Synthesis of DNA in Vitro via a Polymerase–Catalyzed Chain Reaction," Methods in Enzymology 155:335–350 (1987).
Naif et al., "Early Detection of Bovine Leukemia Virus by Using an Enzyme–Linked Assay for Polymerase Chain Reaction–Amplified Proviral DNA in Experimentally Infected Cattle," J. Vlin. Microbiology 30:675–679 (1992).
Reiter et al., "Global and Local Genome Mapping in Arabidopsis thaliana by using Recombinant Inbred Lines and Random Amplified Polymorphic DNAs," Proc. Natl. Acad. Sci. USA 89:1477–1481 (1992).
Saiki et al., "Genetic Analysis of Amplified DNA with Immobilized Sequence–Specific Oligonucleotide probes," Proc. Natl. Acad. Sci. USA 86:6230–6234 (1989).
Williams et al., "Restriction Fragment Length Polymorphism Analysis of Polymerase Chain Reaction Products Amplified from Mapped Loci of Rice (Oryza sativa L.,) Genomic DNA," Theor. Appl. Genet. 82:489–498 (1991).
Ho et al., "Site Directed Mutagenesis by Overlap Extension Using the Polymerase Chain Reaction," Gene 7:51–59 (1989).
Mamotte et al., "A Robust Strategy for Screening and Confirmation of Familial Defective Apolipoprotein B–100," Clinical Chemistry 39:118–121 (1993).
Ugozzoli., "Detection of Specific Alleles by Using Allele–specific Primer Extension Followed by Capture on Solid Support," GATA 9:107–112 (1992).
Fujimoto et al., "PCR–Based Restriction Fragment Length Polymerism Typing of *Heliobacter*Pylori," J. Clin. Microbiology 32:331–334, 1994.

*Primary Examiner*—Kenneth R. Horlick
*Assistant Examiner*—Jeffrey Siew
*Attorney, Agent, or Firm*—Clark & Elbing LLP

[57] ABSTRACT

The invention features methods for detecting polymorphic restriction sites in nucleic acids and kits for carrying out these methods.

66 Claims, 12 Drawing Sheets

CLEAVED AMPLIFIED RFLP DETECTION METHODS

This application is a continuation-in-part of U.S. Ser. No. 08/210,226, filed on Mar. 18, 1994, now abandoned, and PCT/US95/03419 filed Mar. 17, 1995.

This invention was made with Government support under Contract No. GM 48707 awarded by the National Institutes of Health and Contract No. MCB-9406240 awarded by the National Science Foundation. The Government has certain rights in the invention.

BACKGROUND OF THE INVENTION

This invention relates to the generation and detection of genetic polymorphisms.

Genetic maps consisting primarily of restriction fragment length polymorphic (RFLP) markers are being constructed for many organisms, including man. Traditional approaches for detecting RFLPs involve Southern blot hybridization. Recently, techniques based on the polymerase chain reaction (PCR; Mullis et al., Methods Enzymol. 155:350–355, 1987) have been used in addition to, or in place of, traditional RFLP markers in genetic analysis (Cox et al., BioEssays 13:193–198, 1991). In contrast to traditional RFLP markers, PCR-generated markers can be scored using a small sample of DNA, without the use of radioactivity, and without the need for time-consuming DNA blotting procedures.

One widely used PCR-based approach involves the use of single short PCR primers of arbitrary sequence called RAPD primers (for random Amplified polymorphic DNA; Reiter et al., Proc. Natl. Acad. Sci. USA 89:1477–1481, 1992; Williams et al., Theoret. Appl. Genet. 82:489–498, 1991). A second category of PCR-based markers are called SSLPs (for simple sequence length polymorphism). The method employing SSLPs is based on amplification across tandem repeats of one or a few nucleotides known as "microsatellites." Microsatellites occur frequently and randomly in most eukaryotic genomes and display a high degree of polymorphism due to variation in the numbers of repeated units.

A third category of PCR-based markers are called AFLPs (for amplified fragment length polymorphisms) In the method employing these markers, DNA from two polymorphic strains are cleaved with one or two restriction endonucleases, and adapters are ligated to the ends of the cleaved fragments. The fragments are then amplified using primers complementary to the adapter(s). The primers contain short stretches of random nucleotides at their 3' ends, which result in limiting the number of amplified fragments generated.

SUMMARY OF THE INVENTION

We have developed novel PCR-based methods for detecting the presence or absence of a polymorphic restriction site in a nucleic acid involving the use of differentially labeled PCR primers and oligonucleotides.

Accordingly, in one aspect, the invention features a method for detecting the presence or absence of a polymorphic restriction site in a nucleic acid, involving the steps of: (a) amplifying the nucleic acid by PCR using a first and a second primer flanking the polymorphic restriction site, the first primer being tagged with the first member of a specific binding pair, the second primer being tagged with a detectable label; (b) digesting the PCR product of step (a) with the restriction endonuclease corresponding to the polymorphic restriction site; (c) contacting the reaction product of step (b) with the second member of the specific binding pair, immobilized on a solid support; and (d) measuring the level of the detectable label bound to the solid support, the presence of the detectable label bound to the solid support being an indication of the absence of the polymorphic restriction site in the nucleic acid.

In a second aspect, the invention features a method for detecting the presence or absence of a polymorphic restriction site in a nucleic acid, involving the steps of: (a) amplifying the nucleic acid by PCR using a first and a second primer flanking the polymorphic restriction site, the first primer being tagged with the first member of a specific binding pair, the second primer being tagged with a first detectable label; (b) digesting the PCR product of step (a) with the restriction endonuclease corresponding to the polymorphic restriction site; (c) annealing and ligating to the single-stranded ends generated in the reaction of step (b) an oligonucleotide tagged with a second detectable label; (d) contacting the reaction product of step (c) with the second member of the specific binding pair, immobilized on a solid support; and (e) determining the levels of the first and second detectable labels bound to the solid support, the presence of only the first detectable label bound to the solid support being an indication of a homozygote lacking the polymorphic restriction site, the presence of only the second detectable label bound to the solid support being an indication of a homozygote containing the polymorphic restriction site, and the presence of both the first and second detectable labels bound to the solid support being an indication of a heterozygote.

In a third aspect, the invention features a method for detecting the presence or absence of a polymorphic restriction site in a nucleic acid, the method involving the steps of: (a) amplifying the nucleic acid by PCR using a first and a second primer flanking the polymorphic restriction site, the first primer being tagged with a detectable label, the second primer being unlabeled; (b) digesting a portion of the reaction of step (a) with the restriction endonuclease corresponding to the polymorphic restriction site, while leaving another portion of the reaction of step (a) undigested; (c) denaturing the digested and undigested portions from step (b); (d) contacting the product of step (c) with an oligonucleotide complementary to a sequence in the strand of the product of step (c) containing the detectable label, the sequence being between the polymorphic restriction and the sequence complementary to the second primer, the oligonucleotide being tagged with a first member of a specific binding pair; (e) contacting the reaction product of step (d) with the second member of the specific binding pair, immobilized on a solid support; and (f) determining the ratio of the levels of the detectable label bound to the solid support between undigested and digested samples, a ratio of 1:0 between equivalent portions of the undigested and digested samples being an indication of a homozygote containing the polymorphic restriction site, a ratio of 1:1 between equivalent portions of the undigested and digested samples being an indication of a homozygote lacking the polymorphic restriction site, and a ratio of 2:1 between equivalent portions of the undigested and digested samples being an indication of a heterozygote.

In a fourth aspect, the invention features a method for detecting the presence or absence of a polymorphic restriction site in a nucleic acid, involving the steps of: (a) amplifying the nucleic acid by PCR using a first and a second primer flanking the polymorphic restriction site, the first primer being tagged with a first detectable label, the second primer being tagged with a second detectable label;

(b) digesting the reaction product of step (a) with the restriction endonuclease corresponding to the polymorphic restriction site; (c) denaturing the reaction product of step (b); (d) contacting the product of step (c) with a first and a second oligonucleotide, the first oligonucleotide being complementary to a first sequence in the strand of the product of step (c) containing the first detectable label, the first sequence being between the polymorphic restriction site and the sequence corresponding to the first primer, the first oligonucleotide being tagged with the first member of a first specific binding pair, the second oligonucleotide being complementary to a second sequence in the strand of the product of step (c) containing the second detectable label, the second sequence being on the same side of the polymorphic restriction site as the first sequence, the second sequence not being contained within or being complementary to either of the first or second primers, the second oligonucleotide being tagged with the first member of a second specific binding pair; (e) contacting a first portion of the reaction product of step (d) with the second member of the first specific binding pair, immobilized on a first solid support; (f) contacting a second portion of the reaction product of step (d) with the second member of the second specific binding pair, immobilized on a second solid support; and (g) determining the ratio of the levels of the first and second detectable labels bound to the first and second solid supports, a ratio of 1:0 between equivalent amounts of the first and second portions being an indication of a homozygote containing the polymorphic restriction site, a ratio of 1:1 between equivalent amounts of the first and second portions being an indication of a homozygote lacking the polymorphic restriction site, and a ratio of 2:1 between equivalent amounts of the first and second portions being an indication of a heterozygote.

In a fifth aspect, the invention features a method for detecting the presence or absence of a polymorphic restriction site in a nucleic acid, involving the steps of: (a) amplifying the nucleic acid by PCR using a first and a second primer flanking the polymorphic restriction site, the first primer being tagged with a first detectable label, the second primer being tagged with a second detectable label; (b) digesting the reaction product of step (a) with the restriction endonuclease corresponding to the polymorphic restriction site; (c) denaturing the reaction product of step (b); (d) contacting the product of step (c) with a first and a second oligonucleotide, the first oligonucleotide being complementary to a first sequence in the strand of the product of step (c) containing the first detectable label, the first sequence being between the polymorphic restriction site and the sequence complementary to the second primer, the first oligonucleotide being tagged with the first member of a first specific binding pair, the second oligonucleotide being complementary to a second sequence in the strand of the product of step (c) containing the second detectable label, the second sequence being on the same side of the polymorphic restriction site as the first sequence, the second sequence not being contained within or being complementary to either of the first or second primers, the second oligonucleotide being tagged with the first member of a second specific binding pair; (e) contacting a first portion of the reaction product of step (d) with the second member of the first specific binding pair, immobilized on a first solid support; (f) contacting a second portion of the reaction product of step (d) with the second member of the second specific binding pair, immobilized on a second solid support; and (g) determining the ratio of the levels of the first and second detectable labels bound to the first and second solid supports, a ratio of 0:1 between equivalent amounts of the first and second portions being an indication of a homozygote containing the polymorphic restriction site, a ratio of 1:1 between equivalent amounts of the first and second portions being an indication of a homozygote lacking the polymorphic restriction site, and a ratio of 1:2 between equivalent amounts of the first and second portions being an indication of a heterozygote.

In a sixth aspect, the invention method for detecting the presence or absence of a polymorphic restriction site in a nucleic acid, involving the steps of: (a) amplifying the nucleic acid by PCR using a first and a second primer flanking the polymorphic restriction site, the first primer being tagged with a first detectable label, the second primer being tagged with a second detectable label; (b) digesting the reaction product of step (a) with the restriction endonuclease corresponding to the polymorphic restriction site; (c) denaturing the reaction product of step (b); (d) contacting the product of step (c) with a first and a second oligonucleotide, the first oligonucleotide being complementary to a first sequence in the strand of the product of step (c) containing the first detectable label, the first sequence being between the polymorphic restriction site and the sequence corresponding to the first primer, the first oligonucleotide being tagged with the first member of a specific binding pair, the second oligonucleotide being complementary to a second sequence in the strand of the product of step (c) containing the second detectable label, the second sequence being on the same side of the polymorphic restriction site as the first sequence, the second sequence not being contained within or being complementary to either of the first or second primers, the second oligonucleotide being tagged with the first member of the specific binding pair; (e) contacting the reaction product of step (d) with the second member of the specific binding pair, immobilized on a solid support; and (f) determining the ratio of the levels of the first and second detectable labels bound to the solid support, a ratio of 1:0 being an indication of a homozygote containing the polymorphic restriction site, a ratio of 1:1 being an indication of a homozygote lacking the polymorphic restriction site, and a ratio of 2:1 being an indication of a heterozygote.

In a seventh aspect, the invention features a method for detecting the presence or absence of a polymorphic restriction site in a nucleic acid, involving the steps of: (a) amplifying the nucleic acid by PCR using a first and a second primer flanking the polymorphic restriction site, the first primer being tagged with a first detectable label, the second primer being tagged with a second detectable label; (b) digesting the reaction product of step (a) with the restriction endonuclease corresponding to the polymorphic restriction site; (c) denaturing the reaction product of step (b); (d) contacting the product of step (c) with a first and a second oligonucleotide, the first oligonucleotide being complementary to a first sequence in the strand of the product of step (c) containing the first detectable label, the first sequence being between the polymorphic restriction site and the sequence complementary to the second primer, the first oligonucleotide being tagged with the first member of a specific binding pair, the second oligonucleotide being complementary to a second sequence in the strand of the product of step (c) containing the second detectable label, the second sequence being on the same side of the polymorphic restriction site as the first sequence, the second sequence not being contained within or being complementary to either of the first or second primers, the second oligonucleotide being tagged with the first member of the specific binding pair; (e) contacting the reaction product of step (d) with the second member of the specific binding pair, immobilized on a solid support; and (f) determining the ratio of the levels of the first and second detectable labels bound to the solid support, a ratio of 0:1 being an indication of a homozygote containing the polymorphic restriction site, a ratio of 1:1 being an indication of a homozygote lacking the polymorphic restriction site, and a ratio of 1:2 being an indication of a heterozygote.

In an eighth aspect, the invention features a method for detecting the presence or absence of a polymorphic restriction site in a nucleic acid, involving the steps of: (a) amplifying the nucleic acid by PCR using a first and a second primer flanking the polymorphic restriction site, the first primer being tagged with the first member of a first specific binding pair, the second primer being tagged with a detectable label; (b) digesting the reaction product of step (a) with the restriction endonuclease corresponding to the polymorphic restriction site; (c) contacting the reaction product of step (b) with the second member of the first specific binding pair, immobilized on a first solid support; (d) denaturing the reaction product of step (c) not bound to the first solid support; (e) contacting the product of step (d) with an oligonucleotide complementary to a sequence in the strand of the product of step (d) containing the detectable label, the sequence being between the polymorphic restriction site and the sequence corresponding to the second primer, the oligonucleotide being tagged with the first member of a second specific binding pair; (f) contacting the reaction product of step (e) with the second member of the second specific binding pair, immobilized on a second solid support; and (g) determining the ratio of the level of the detectable label bound to the first solid support to the level of the detectable label bound to the second solid support, a ratio of 0:1 being an indication of a homozygote containing the polymorphic restriction site, in a case where the total amount of the reaction product from step (c) not bound to the first solid support was used in steps (d), (e), and (f); a ratio of 1:0 being an indication of a homozygote lacking the polymorphic restriction site, in a case where the total amount of the reaction product from step (c) not bound to the first solid support was used in steps (d), (e), and (f); and a ratio of 1:1 being an indication of a heterozygote, in a case where the total amount of the reaction product from step (c) not bound to the first solid support was used in steps (d), (e), and (f). In a ninth aspect, the invention features a method for detecting the presence or absence of a polymorphic restriction site in a nucleic acid, involving the steps of: (a) amplifying the nucleic acid by PCR using a first and a second primer flanking the polymorphic restriction site, the first primer being tagged with a detectable label, the second primer being unlabeled; (b) digesting the reaction product of step (a) with the restriction endonuclease corresponding to the polymorphic restriction site; (c) annealing and ligating to the single-stranded ends generated in the reaction of step (b) a first oligonucleotide tagged with the first member of a first specific binding pair; (d) contacting the reaction product of step (c) with the second member of the first specific binding pair, immobilized on a first solid support; (e) denaturing the reaction product of step (d) not bound to the first solid support; (f) contacting the product of step (e) with a second oligonucleotide complementary to a sequence in the strand of the product of step (e) containing the detectable label, the sequence being between the polymorphic restriction site and either the sequence corresponding to the first primer or the sequence complementary to the second primer, the second oligonucleotide being tagged with the first member of a second specific binding pair; (g) contacting the reaction product of step (f) with the second member of the second specific binding pair, immobilized on a second solid support; and (h) determining the ratio of the level of the detectable label bound to the first solid support to the level of the detectable label bound to the second solid support, a ratio of 1:0 being an indication of a homozygote containing the polymorphic restriction site, in a case where the total amount of the reaction product from step (d) not bound to the first solid support was used in steps (e), (f), and (g); a ratio of 0:1 being an indication of a homozygote lacking the polymorphic restriction site, in a case where the total amount of the reaction product from step (d) not bound to the first solid support was used in steps (e), (f), and (g); and a ratio of 1:1 being an indication of a heterozygote; in a case where the total amount of the reaction product from step (d) not bound to the first solid support was used in steps (e), (f), and (g).

In a tenth aspect, the invention features a method for detecting the presence or absence of a polymorphic restriction site in a nucleic acid, involving the steps of: (a) amplifying the nucleic acid by PCR using a first and a second primer flanking the polymorphic restriction site, the first primer being tagged with the first member of a first specific binding pair, the second primer being tagged with a detectable label; (b) digesting the reaction product of step (a) with the restriction endonuclease corresponding to the polymorphic restriction site; (c) contacting the reaction product of step (b) with the second member of the first specific binding pair, immobilized on a first solid support; (d) denaturing the reaction product from step (c) not bound to the first solid support; (e) contacting the product of step (d) with an oligonucleotide complementary to a sequence in the strand of the product of step (d) containing the detectable label, the sequence being between the polymorphic restriction site and the sequence corresponding to the second primer, the oligonucleotide being immobilized on a second solid support; and (f) determining the ratio of the level of the detectable label bound to the first solid support to the level of the detectable label bound to the second solid support, a ratio of 0:1 being an indication of a homozygote containing the polymorphic restriction site, in a case where the total amount of the reaction product from step (c) not bound to the first solid support was used in steps (d) and (e); a ratio of 1:0 being an indication of a homozygote lacking the polymorphic restriction site, in a case where the total amount of the reaction product from step (c) not bound to the first solid support was used in steps (d) and (e); and a ratio of 1:1 being an indication of a heterozygote, in a case where the total amount of the reaction product from step (c) not bound to the first solid support was used in steps (d) and (e).

In an eleventh aspect, the invention features a method for detecting the presence or absence of a polymorphic restriction site in a nucleic acid, involving the steps of: (a) amplifying the nucleic acid by PCR using a first and a second primer flanking the polymorphic restriction site, the first primer being tagged with a detectable label, the second primer being unlabeled; (b) digesting the reaction product of step (a) with the restriction endonuclease corresponding to the polymorphic restriction site; (c) annealing and ligating to the single-stranded ends generated in the reaction of step (b) a first oligonucleotide tagged with the first member of a first specific binding pair; (d) contacting the reaction product of step (c) with the second member of the first specific binding pair, immobilized on a first solid support; (e) denaturing the reaction product of step (d) not bound to the first solid support; (f) contacting the product of step (e) with a second oligonucleotide complementary to a sequence in the strand of the product of step (e) containing the detectable label, the sequence being between the polymorphic restriction site and either the sequence corresponding to the first primer or the sequence complementary to the second primer, the second oligonucleotide being immobilized on a second solid support; and (g) determining the ratio of the level of the detectable label bound to the first solid support to the level of the detectable label bound to the second solid support, a ratio of 1:0 being an indication of a homozygote containing the polymorphic restriction site, in a case where the total amount of the reaction product from step (d) not bound to the first solid support was used in steps (e) and (f); a ratio of 0:1 being an indication of a homozygote lacking the polymorphic restriction site, in a case where the total amount of the reaction product from step (d) not bound to the first solid support was used in steps (e) and (f); and a ratio of 1:1 being an indication of a heterozygote, in a case where the total amount of the reaction product from step (d) not bound to the first solid support was used in steps (e) and (f).

In a twelfth aspect, the invention features a method for detecting the presence or absence of a polymorphic restriction site in a nucleic acid, involving the steps of: (a) amplifying the nucleic acid by PCR using a first and a second primer flanking the polymorphic restriction site, the first primer containing a first sequence not complementary to or present in the nucleic acid, the second primer containing a second sequence not complementary to or present in the nucleic acid; (b) amplifying the product of step (a) by PCR using a third and a fourth primer, the third primer containing the first sequence or a sequence complementary to the first sequence, the third primer being tagged with the first member of a specific binding pair, the fourth primer containing the second sequence or a sequence complementary to the second sequence, the fourth primer being tagged with a detectable label; (c) digesting the product of step (b) with the restriction endonuclease corresponding to the polymorphic restriction site; (d) contacting the reaction product of step (c) with the second member of the specific binding pair, immobilized on a solid support; and (e) measuring the level of the detectable label bound to the solid support, the presence of the detectable label bound to the solid support being an indication of the absence of the polymorphic restriction site in the nucleic acid.

In a thirteenth aspect, the invention features a method for detecting the presence or absence of a polymorphic restriction site in a nucleic acid, involving the steps of: (a) amplifying the nucleic acid by PCR using a first and a second primer flanking the polymorphic restriction site, the first primer containing a first sequence not complementary to or present in the nucleic acid, the second primer containing a second sequence not complementary to or present in the nucleic acid; (b) amplifying the product of step (a) by PCR using a third and a fourth primer, the third primer containing the first sequence or a sequence complementary to the first sequence, the third primer being tagged with the first member of a specific binding pair, the fourth primer containing the second sequence or a sequence complementary to the second sequence, the fourth primer being tagged with a detectable label; (c) digesting the PCR product of step (b) with the restriction endonuclease corresponding to the polymorphic restriction site; (d) annealing and ligating to the single-stranded ends generated in the reaction of step (c) an oligonucleotide tagged with a second detectable label; (e) contacting the reaction product of step (d) with the second member of the specific binding pair, immobilized on a solid support; and (f) determining the levels of the first and second detectable labels bound to the solid support, the presence of only the first detectable label bound to the solid support being an indication of a homozygote lacking the polymorphic restriction site, the presence of only the second detectable label bound to the solid support being an indication of a homozygote containing the polymorphic restriction site, and the presence of both the first and second detectable labels bound to the solid support being an indication of a heterozygote.

In a fourteenth aspect, the invention features a method for detecting the presence or absence of a polymorphic restriction site in a nucleic acid, involving the steps of: (a) amplifying the nucleic acid by PCR using a first and a second primer flanking the polymorphic restriction site, the first primer containing a first sequence not complementary to or present in the nucleic acid; (b) amplifying the product of step (a) by PCR using a third primer and the second primer, the third primer containing the first sequence, the third primer being tagged with a detectable label; (c) digesting a portion of the reaction of step (b) with the restriction endonuclease corresponding to the polymorphic restriction site, while leaving another portion of the reaction of step (b) undigested; (d) denaturing the digested and undigested portions from step (c); (e) contacting the product of step (d) with an oligonucleotide complementary to a second sequence in the strand of the product of step (d) containing the detectable label, the second sequence being between the polymorphic restriction site and the sequence complementary to the second primer, the oligonucleotide being tagged with a first member of a specific binding pair; (f) contacting the reaction product of step (e) with the second member of the specific binding pair, immobilized on a solid support; and (g) determining the ratio of the levels of the detectable label bound to the solid support between undigested and digested samples, a ratio of 1:0 between equivalent portions of the undigested and digested samples being an indication of a homozygote containing the polymorphic restriction site, a ratio of 1:1 between equivalent portions of the undigested and digested samples being an indication of a homozygote lacking the polymorphic restriction site, and a ratio of 2:1 between equivalent portions of the undigested and digested samples being an indication of a heterozygote.

In a fifteenth aspect, the invention features a method for detecting the presence or absence of a polymorphic restriction site in a nucleic acid, involving the steps of: (a) amplifying the nucleic acid by PCR using a first and a second primer flanking the polymorphic restriction site, the first primer containing a first sequence not complementary to or present in the nucleic acid, the second primer containing a second sequence not complementary to or present in the nucleic acid; (b) amplifying the product of step (a) by PCR using a third and a fourth primer, the third primer containing the first sequence or a sequence complementary to the first sequence, the third primer being tagged with a first detectable label, the fourth primer containing the second sequence or a sequence complementary to the second sequence, the fourth primer being tagged with a second detectable label; (c) digesting the reaction product of step (b) with the restriction endonuclease corresponding to the polymorphic restriction site; (d) denaturing the reaction product of step (c); (e) contacting the product of step (d) with a first and a second oligonucleotide, the first oligonucleotide being complementary to a third sequence in the strand of the product of step (d) containing the first detectable label, the third sequence being between the polymorphic restriction site and the sequence corresponding to or complementary to the first primer, the first oligonucleotide being tagged with the first member of a first specific binding pair, the second oligonucleotide being complementary to a fourth sequence in the strand of the product of step (d) containing the second detectable label, the fourth sequence being on the same side of the polymorphic restriction site as the third sequence, the fourth sequence not being contained within or being complementary to any of the primers, the second oligonucleotide being tagged with the first member of a second specific binding pair; (f) contacting a first portion of the reaction product of step (e) with the second member of the first specific binding pair, immobilized on a first solid support; (g) contacting a second portion of the reaction product of step (e) with the second member of the second specific binding pair, immobilized on a second solid support; and (h) determining the ratio of the levels of the first and second detectable labels bound to the first and second solid supports, a ratio of 1:0 between equivalent amounts of the first and second portions being an indication of a homozygote containing the polymorphic restriction site, a ratio of 1:1 between equivalent amounts of the first and second portions being an indication of a homozygote lacking the polymorphic restriction site, and a ratio of 2:1 between equivalent amounts of the first and second portions being an indication of a heterozygote.

In a sixteenth aspect, the invention features a method for detecting the presence or absence of a polymorphic restriction site in a nucleic acid, involving the steps of: (a) amplifying the nucleic acid by PCR using a first and a second primer flanking the polymorphic restriction site, the first primer containing a first sequence not complementary to or present in the nucleic acid, the second primer containing a second sequence not complementary to or present in the nucleic acid; (b) amplifying the product of step (a) by PCR using a third and a fourth primer, the third primer containing the first sequence or a sequence complementary to the first sequence, the third primer being tagged with a first detectable label, the fourth primer containing the second sequence or a sequence complementary to the second sequence, the fourth primer being tagged with a second detectable label; (c) digesting the reaction product of step (b) with the restriction endonuclease corresponding to the polymorphic restriction site; (d) denaturing the reaction product of step (c); (e) contacting the product of step (d) with a first and a second oligonucleotide, the first oligonucleotide being complementary to a third sequence in the strand of the product of step (d) containing the first detectable label, the third sequence being between the polymorphic restriction site and the sequence corresponding to or complementary to the second primer, the first oligonucleotide being tagged with the first member of a first specific binding pair, the second oligonucleotide being complementary to a fourth sequence in the strand of the product of step (d) containing the second detectable label, the fourth sequence being on the same side of the polymorphic restriction site as the third sequence, the fourth sequence not being contained within or being complementary to any of the primers, the second oligonucleotide being tagged with the first member of a second specific binding pair; (f) contacting a first portion of the reaction product of step (e) with the second member of the first specific binding pair, immobilized on a first solid support; (g) contacting a second portion of the reaction product of step (e) with the second member of the second specific binding pair, immobilized on a second solid support; and (h) determining the ratio of the levels of the first and second detectable labels bound to the first and second solid supports, a ratio of 0:1 between equivalent amounts of the first and second portions being an indication of a homozygote containing the polymorphic restriction site, a ratio of 1:1 between equivalent amounts of the first and second portions being an indication of a homozygote lacking the polymorphic restriction site, and a ratio of 1:2 between equivalent amounts of the first and second portions being an indication of a heterozygote.

In a seventeenth aspect, the invention features a method for detecting the presence or absence of a polymorphic restriction site in a nucleic acid, involving the steps of: (a) amplifying the nucleic acid by PCR using a first and a second primer flanking the polymorphic restriction site, the first primer containing a first sequence not complementary to or present in the nucleic acid, the second primer containing a second sequence not complementary to or present in the nucleic acid; (b) amplifying the product of step (a) by PCR using a third and a fourth primer, the third primer containing the first sequence or a sequence complementary to the first sequence, the third primer being tagged with a first detectable label, the fourth primer containing the second sequence or a sequence complementary to the second sequence, the fourth primer being tagged with a second detectable label; (c) digesting the reaction product of step (b) with the restriction endonuclease corresponding to the polymorphic restriction site; (d) denaturing the reaction product of step (c); (e) contacting the product of step (d) with a first and a second oligonucleotide, the first oligonucleotide being complementary to a third sequence in the strand of the product of step (d) containing the first detectable label, the third sequence being between the polymorphic restriction site and the sequence corresponding to or complementary to the first primer, the first oligonucleotide being tagged with the first member of a specific binding pair, the second oligonucleotide being complementary to a fourth sequence in the strand of the product of step (d) containing the second detectable label, the fourth sequence being on the same side of the polymorphic restriction site as the third sequence, the fourth sequence not being contained within or being complementary to any of the primers the second oligonucleotide being tagged with the first member of the specific binding pair; (f) contacting the reaction product of step (e) with the second member of the specific binding pair, immobilized on a solid support; and (g) determining the ratio of the levels of the first and second detectable labels bound to the solid support, a ratio of 1:0 being an indication of a homozygote containing the polymorphic restriction site, a ratio of 1:1 being an indication of a homozygote lacking the polymorphic restriction site, and a ratio of 2:1 being an indication of a heterozygote.

In an eighteenth aspect, the invention features a method for detecting the presence or absence of a polymorphic restriction site in a nucleic acid, involving (a) amplifying the nucleic acid by PCR using a first and second primer flanking the polymorphic restriction site, the first primer containing a first sequence not complementary to or present in the nucleic acid, the second primer containing a second sequence not complementary to or present in the nucleic acid; (b) amplifying the product of step (a) by PCR using a third and a fourth primer, the third primer containing the first sequence or a sequence complementary to the first sequence, the third primer being tagged with a first detectable label, the fourth primer containing the second sequence or a sequence complementary to the second sequence, the fourth primer being tagged with a second detectable label; (c) digesting the reaction product of step (b) with the restriction endonuclease corresponding to the polymorphic restriction site; (d) denaturing the reaction product of step (c); (e) contacting the product of step (d) with a first and a second oligonucleotide, the first oligonucleotide being complementary to a third sequence in the strand of the product of step (d) containing the first detectable label, the third sequence being between the polymorphic restriction site and the sequence corresponding to or complementary to the second primer, the first oligonucleotide being tagged with the first member of a specific binding pair, the second oligonucleotide being complementary to a fourth sequence in the strand of the product of step (d) containing the second detectable label, the fourth sequence being on the same side of the polymorphic restriction site as the third sequence, the fourth sequence not being contained within or being complementary to any of the primers, the second oligonucleotide being tagged with the first member of the specific binding pair; (f) contacting the reaction product of step (e) with the second member of the specific binding pair, immobilized on a solid support; and (g) determining the ratio of the levels of the first and second detectable labels bound to the solid support, a ratio of 0:1 being an indication of a homozygote containing the polymorphic restriction site, a ratio of 1:1 being an indication of a homozygote lacking the polymorphic restriction site, and a ratio of 1:2 being an indication of a heterozygote.

In a nineteenth aspect, the invention features a method for detecting the presence or absence of a polymorphic restriction site in a nucleic acid, involving the steps of (a) amplifying the nucleic acid by PCR using a first and a second primer flanking the polymorphic restriction site, the first primer containing a first sequence not complementary to or present in the nucleic acid, the second primer containing a second sequence not complementary to or present in the nucleic acid; (b) amplifying the product of step (a) by PCR using a third and a fourth primer, the third primer containing the first sequence or a sequence complementary to the first sequence, the third primer being tagged with the first member of a first specific binding pair, the fourth primer containing the second sequence or a sequence complementary to the second sequence, the fourth primer being tagged with a detectable label; (c) digesting the reaction product of step (b) with the restriction endonuclease corresponding to the polymorphic restriction site; (d) contacting the reaction product of step (c) with the second member of the first specific binding pair, immobilized on a first solid support; (e) denaturing the reaction product of step (d) not bound to the first solid support; (f) contacting the product of step (e) with an oligonucleotide complementary to a third sequence in the strand of the product of step (e) containing the detectable label, the third sequence being between the polymorphic restriction site and the sequence corresponding to or complementary to the second primer, the oligonucleotide being tagged with the first member of a second specific binding pair; (g) contacting the reaction product of step (f) with the second member of the second specific binding pair, immobilized on a second solid support; and (h) determining the ratio of the level of the detectable label bound to the first solid support to the level of the detectable label bound to the second solid support, a ratio of 0:1 being an indication of a homozygote containing the polymorphic restriction site, in a case where the total amount of the reaction product from step (d) not bound to the first solid support was used in steps (e), (f), and (g); a ratio of 1:0 being an indication of a homozygote lacking the polymorphic restriction site, in a case where the total amount of the reaction product from step (d) not bound to the first solid support was used in steps (e), (f), and (g); and a ratio of 1:1 being an indication of a heterozygote, in a case where the total amount of the reaction product from step (d) not bound to the first solid support was used in steps (e), (f), and (g).

In a twentieth aspect the invention features a method for detecting the presence or absence of a polymorphic restriction site in a nucleic acid, involving the steps of: (a) amplifying the nucleic acid by PCR using a first and a second primer flanking the polymorphic restriction site, the first primer containing a first sequence not complementary to or present in the nucleic acid; (b) amplifying the product of step (a) by PCR using a third primer and the second primer, the third primer containing the first sequence, the third primer being tagged with a detectable label; (c) digesting the reaction product of step (b) with the restriction endonuclease corresponding to the polymorphic restriction site; (d) annealing and ligating to the single-stranded ends generated in the reaction of step (c) a first oligonucleotide tagged with the first member of a first specific binding pair; (e) contacting the reaction product of step (d) with the second member of the first specific binding pair, immobilized on a first solid support; (f) denaturing the reaction product of step (e) not bound to the first solid support; (g) contacting the product of step (f) with a second oligonucleotide complementary to a second sequence in the strand of the product of step (f) containing the detectable label, the second sequence being between the polymorphic restriction site and either the sequence corresponding to or complementary to the second primer or the sequence corresponding to or complementary to the first primer, the second oligonucleotide being tagged with the first member of a second specific binding pair; (h) contacting the reaction product of step (g) with the second member of the second specific binding pair, immobilized on a second solid support; and (i) determining the ratio of the level of the detectable label bound to the first solid support to the level of the detectable label bound to the second solid support, a ratio of 1:0 being an indication of a homozygote containing the polymorphic restriction site, in a case where the total amount of the reaction product from step (e) not bound to the first solid support was used in steps (f), (g), and (h); a ratio of 0:1 being an indication of a homozygote lacking the polymorphic restriction site, in a case where the total amount of the reaction product from step (e) not bound to the first solid support was used in steps (f), (g), and (h); and a ratio of 1:1 being an indication of a heterozygote; in a case where the total amount of the reaction product from step (e) not bound to the first solid support was used in steps (f), (g), and (h).

In a twenty-first aspect, the invention features a method for detecting the presence or absence of a polymorphic restriction site in a nucleic acid, involving the steps of: (a) amplifying the nucleic acid by PCR using a first and a second primer flanking the polymorphic restriction site, the first primer containing a first sequence not complementary to or present in the nucleic acid, the second primer containing a second sequence not complementary to or present in the nucleic acid; (b) amplifying the product of step (a) by PCR using a third and a fourth primer, the third primer containing the first sequence or a sequence complementary to the first sequence, the third primer being tagged with the first member of a first specific binding pair, the fourth primer containing the second sequence or a sequence complementary to the second sequence, the fourth primer being tagged with a detectable label; (c) digesting the reaction product of step (b) with the restriction endonuclease corresponding to the polymorphic restriction site; (d) contacting the reaction product of step (c) with the second member of the first specific binding pair, immobilized on a first solid support; (e) denaturing the reaction product from step (d) not bound to the first solid support; (f) contacting the product of step (e) with an oligonucleotide complementary to a third sequence in the strand of the product of step (e) containing the detectable label, the third sequence being between the polymorphic restriction site and the sequence corresponding to or complementary to the second primer, the oligonucleotide being immobilized on a second solid support; and (g) determining the ratio of the level of the detectable label bound to the first solid support to the level of the detectable label bound to the second solid support, a ratio of 0:1 being an indication of a homozygote containing the polymorphic restriction site, in a case where the total amount of the reaction product from step (d) not bound to the first solid support was used in steps (e) and (f); a ratio of 1:0 being an indication of a homozygote lacking the polymorphic restriction site, in a case where the total amount of the reaction product from step (d) not bound to the first solid support was used in steps (e) and (f); and a ratio of 1:1 being an indication of a heterozygote, in a case where the total amount of the reaction product from step (d) not bound to the first solid support was used in steps (e) and (f).

In a twenty-second aspect, the invention features a method for detecting the presence or absence of a polymorphic restriction site in a nucleic acid, the method involving the steps of: (a) amplifying the nucleic acid by PCR using a first and a second primer flanking the polymorphic restriction site, the first primer containing a first sequence not complementary to or present in the nucleic acid; (b) amplifying the product of step (a) by PCR using a third primer and the second primer, the third primer containing the first sequence, the third primer being tagged with a detectable label; (c) digesting the reaction product of step (b) with the restriction endonuclease corresponding to the polymorphic restriction site; (d) annealing and ligating to the single-stranded ends generated in the reaction of step (c) a first oligonucleotide tagged with the first member of a first specific binding pair; (e) contacting the reaction product of step (d) with the second member of the first specific binding pair, immobilized on a first solid support; (f) denaturing the reaction product of step (e) not bound to the first solid support; (g) contacting the product of step (f) with a second oligonucleotide complementary to a second sequence in the strand of the product of step (f) containing the detectable label, the second sequence being between the polymorphic restriction site and either the sequence corresponding to or complementary to the second primer or the sequence corresponding to or complementary to the first primer, the second oligonucleotide being immobilized on a second solid support; and (h) determining the ratio of the level of the detectable label bound to the first solid support to the level of the detectable label bound to the second solid support, a ratio of 1:0 being an indication of a homozygote containing the polymorphic restriction site, in a case where the total amount of the reaction product from step (e) not bound to the first solid support was used in steps (f) and (g); a ratio of 0:1 being an indication of a homozygote lacking the polymorphic restriction site, in a case where the total amount of the reaction product from step (e) not bound to the first solid support was used in steps (f) and (g); and a ratio of 1:1 being an indication of a heterozygote, in a case where the total amount of the reaction product from step (e) not bound to the first solid support was used in steps (f) and (g).

In a twenty-third aspect, the invention features a kit for detecting the presence or absence of a polymorphic restriction site in a nucleic acid, the kit containing one or more sets of a first and a second primer flanking the polymorphic restriction site, the first primer being tagged with the first member of a specific binding pair, the second primer being tagged with a detectable label. In a preferred embodiment, the kit further contains the second member of the specific binding pair, immobilized on a solid support. In another preferred embodiment, the kit further contains an oligonucleotide complementary to the single-stranded ends generated in the nucleic acid upon digestion of the nucleic acid with the restriction enzyme corresponding to the polymorphic restriction site, the oligonucleotide being tagged with a second detectable label.

In a twenty-fourth aspect, the invention features a kit for detecting the presence or absence of a polymorphic restriction site in a nucleic acid, the kit containing: (a) a first and a second primer flanking the polymorphic restriction site, the first primer being tagged with a detectable label, the second primer being unlabeled; (b) an oligonucleotide complementary to a sequence in the strand of the nucleic acid complementary to the second primer, the sequence being between the polymorphic restriction site and the sequence complementary to the second primer, the oligonucleotide being tagged with a first member of a specific binding pair; and (c) the second member of the specific binding pair, immobilized on a solid support.

In a twenty-fifth aspect, the invention features a kit for detecting the presence or absence of a polymorphic restriction site in a nucleic acid, the kit containing: (a) a first and a second primer flanking the polymorphic restriction site, the first primer being tagged with a first detectable label, the second primer being tagged with a second detectable label; (b) a first oligonucleotide, the first oligonucleotide being complementary to a first sequence in the strand of the nucleic acid complementary to the second primer, the first sequence being between the polymorphic restriction site and either the sequence corresponding to the first primer or the sequence complementary to the second primer, the first oligonucleotide being tagged with the first member of a first specific binding pair; (c) a second oligonucleotide, the second oligonucleotide being complementary to a second sequence in the strand of the nucleic acid complementary to the first primer, the second sequence being on the same side of the polymorphic restriction site as the first sequence, the second sequence not being contained within or being complementary to either of the first or second primers, the second oligonucleotide being tagged with the first member of a second specific binding pair; (d) the second member of the first specific binding pair, immobilized on a first solid support; and (e) the second member of the second specific binding pair, immobilized on a second solid support. In a preferred embodiment, the first and the second specific binding pairs are identical, and the first and the second solid supports are identical.

In a twenty-sixth aspect, the invention features a kit for detecting the presence or absence of a polymorphic restriction site in a nucleic acid, the kit containing: (a) a first and a second primer flanking the polymorphic restriction site, the first primer being tagged with the first member of a first specific binding pair, the second primer being tagged with a detectable label; (b) the second member of the first specific binding pair, immobilized on a first solid support; (c) an oligonucleotide complementary to a first sequence in the strand of the nucleic acid containing the sequence corresponding to the second primer, the first sequence being between the polymorphic restriction site and the sequence corresponding to the second primer, the oligonucleotide being tagged with the first member of a second specific binding pair; and (d) the second member of the second specific binding pair, immobilized on a second solid support.

In a twenty-seventh aspect, the invention features a kit for detecting the presence or absence of a polymorphic restriction site in a nucleic acid, the kit containing: (a) a first and a second primer flanking the polymorphic restriction site, the first primer being tagged with a detectable label, the second primer being unlabeled; (b) a first oligonucleotide complementary to the single-stranded ends generated in the nucleic acid upon digestion of the nucleic acid with the restriction enzyme corresponding to the polymorphic restriction site, the oligonucleotide being tagged with the first member of a first specific binding pair; (c) the second member of the first specific binding pair, immobilized on a first solid support; (d) a second oligonucleotide complementary to a sequence in the strand of the nucleic acid complementary to the second primer, the sequence being between the polymorphic restriction site and either the sequence corresponding to the first primer or the sequence complementary to the second primer, the second oligonucleotide being tagged with the first member of a second specific binding pair; and (e) the second member of the second specific binding pair, immobilized on a second solid support.

In a twenty-eighth aspect, the invention features a kit for detecting the presence or absence of a polymorphic restriction site in a nucleic acid, the kit containing: (a) a first and a second primer flanking the polymorphic restriction site, the first primer being tagged with the first member of a first specific binding pair, the second primer being tagged with a detectable label; (b) the second member of the first specific binding pair, immobilized on a first solid support; and (c) an oligonucleotide complementary to a first sequence in the strand of the nucleic acid containing the sequence corresponding to the second primer, the first sequence being between the polymorphic restriction site and the sequence corresponding to the second primer, the oligonucleotide being immobilized on a second solid support.

In a twenty-ninth aspect, the invention features a kit for detecting the presence or absence of a polymorphic restriction site in a nucleic acid, the kit containing: (a) a first and a second primer flanking the polymorphic restriction site, the first primer being tagged with a detectable label, the second primer being unlabeled; (b) a first oligonucleotide complementary to the single-stranded ends generated in the nucleic acid upon digestion of the nucleic acid with the restriction enzyme corresponding to the polymorphic restriction site, the oligonucleotide being tagged with the first member of a first specific binding pair; (c) the second member of the first specific binding pair, immobilized on a first solid support; and (d) a second oligonucleotide complementary to a sequence in the strand of the nucleic acid complementary to the second primers the sequence being between the polymorphic restriction site and either the sequence corresponding to the first primer or the sequence complementary to the second primer, the second oligonucleotide being immobilized on a second solid support.

In a thirtieth aspect, the invention features a kit for detecting the presence or absence of a polymorphic restriction site in a nucleic acid, the kit containing: (a) a first and a second primer flanking the polymorphic restriction site, the first primer containing a first sequence not complementary to or present in the nucleic acid, the second primer containing a second sequence not complementary to or present in the nucleic acid; (b) a third and a fourth primer, the third primer containing the first sequence or a sequence complementary to the first sequence, the third primer being tagged with the first member of a specific binding pair, the fourth primer containing the second sequence or a sequence complementary to the second sequence, the fourth primer being tagged with a detectable label. In a preferred embodiment, the kit further contains the second member of the specific binding pair, immobilized on a solid support. In another preferred embodiment, the kit further contains an oligonucleotide complementary to the single-stranded ends generated in the nucleic acid upon digestion of the nucleic acid with the restriction enzyme corresponding to the polymorphic restriction site, the oligonucleotide being tagged with a second detectable label. In a thirty-first aspect, the invention features a kit for detecting the presence or absence of a polymorphic restriction site in a nucleic acid, the kit containing: (a) a first and a second primer flanking the polymorphic restriction site, the first primer containing a first sequence not complementary to or present in the nucleic acid; (b) a third primer containing the first sequence, the third primer being tagged with a detectable label; (c) an oligonucleotide complementary to a second sequence in the strand of the nucleic acid containing the sequence complementary to the second primer, the second sequence being between the polymorphic restriction site and the sequence complementary to the second primer, the oligonucleotide being tagged with a first member of a specific binding pair; and (d) the second member of the specific binding pair, immobilized on a solid support.

In a thirty-second aspect, the invention features a kit for detecting the presence or absence of a polymorphic restriction site in a nucleic acid, the kit containing: (a) a first and a second primer flanking the polymorphic restriction site, the first primer containing a first sequence not complementary to or present in the nucleic acid, the second primer containing a second sequence not complementary to or present in the nucleic acid; (b) a third and a fourth primer, the third primer containing the first sequence or a sequence complementary to the first sequence, the third primer being tagged with a first detectable label, the fourth primer containing the second sequence or a sequence complementary to the second sequence, the fourth primer being tagged with a second detectable label; (c) a first oligonucleotide, the first oligonucleotide being complementary to a third sequence in the strand of the nucleic acid complementary to the second primer, the third sequence being between the polymorphic restriction site and either the sequence complementary to the second primer or the sequence corresponding to the first primer, the first oligonucleotide being tagged with the first member of a first specific binding pair, (d) a second oligonucleotide, the second oligonucleotide being complementary to a fourth sequence in the strand of the nucleic acid complementary to the first primer, the fourth sequence being on the same side of the polymorphic restriction site as the third sequence, the fourth sequence not being contained within or being complementary to any of the primers the second oligonucleotide being tagged with the first member of a second specific binding pair; (e) the second member of the first specific binding pair, immobilized on a first solid support; and (f) the second member of the second specific binding pair, immobilized on a second solid support. In a preferred embodiment, the first and the second specific binding pairs are identical, and the first and the second solid supports are identical.

In a thirty-third aspect, the invention features a kit for detecting the presence or absence of a polymorphic restriction site in a nucleic acid, the kit containing: (a) a first and a second primer flanking the polymorphic restriction site, the first primer containing a first sequence not complementary to or present in the nucleic acid, the second primer containing a second sequence not complementary to or present in the nucleic acid; (b) a third and a fourth primer, the third primer containing the first sequence or a sequence complementary to the first sequence, the third primer being tagged with the first member of a first specific binding pair, the fourth primer containing the second sequence or a sequence complementary to the second sequence, the fourth primer being tagged with a detectable label; (c) the second member of the first specific binding pair, immobilized on a first solid support; (d) an oligonucleotide complementary to a third sequence in the strand of the nucleic acid corresponding to the second primer, the sequence being between the polymorphic restriction site and the sequence corresponding to the second primer, the oligonucleotide being tagged with the first member of a second specific binding pair; and (e) the second member of the second specific binding pair, immobilized on a second solid support.

In a thirty-fourth aspect, the invention features a kit for detecting the presence or absence of a polymorphic restriction site in a nucleic acid, the kit containing: (a) a first and a second primer flanking the polymorphic restriction site, the first primer containing a first sequence not complementary to or present in the nucleic acid; (b) a third primer containing the first sequence, the third primer being tagged with a detectable label; (c) a first oligonucleotide complementary to the single-stranded ends generated in the nucleic acid upon digestion of the nucleic acid with the restriction enzyme corresponding to the polymorphic restriction site, the oligonucleotide being tagged with the first member of a first specific binding pair; (d) the second member of the first specific binding pair, immobilized on a first solid support; (e) a second oligonucleotide complementary to a second sequence in the strand of the nucleic acid corresponding to the first primer, the second sequence being between the polymorphic restriction site and either the sequence complementary to the second primer or the sequence corresponding to the first primer, the second oligonucleotide being tagged with the first member of a second specific binding pair; and (f) the second member of the second specific binding pair, immobilized on a second solid support.

In a thirty-fifth aspect, the invention features a kit for detecting the presence or absence of a polymorphic restriction site in a nucleic acid, the kit containing: (a) a first and a second primer flanking the polymorphic restriction site, the first primer containing a first sequence not complementary to or present in the nucleic acid, the second primer containing a second sequence not complementary to or present in the nucleic acid; (b) a third and a fourth primer, the third primer containing the first sequence or a sequence complementary to the first sequence, the third primer being tagged with the first member of a first specific binding pair, the fourth primer containing the second sequence or a sequence complementary to the second sequence, the fourth primer being tagged with a detectable label; (c) the second member of the first specific binding pair, immobilized on a first solid support; and (d) an oligonucleotide complementary to a third sequence in the strand of the nucleic acid corresponding to the second primer, the third sequence being between the polymorphic restriction site and the sequence corresponding to the second primer, the oligonucleotide being immobilized on a second solid support.

In a thirty-sixth aspect, the invention features a kit for detecting the presence or absence of a polymorphic restriction site in a nucleic acid, the kit containing: (a) a first and a second primer flanking the polymorphic restriction site, the first primer containing a first sequence not complementary to or present in the nucleic acid; (b) a third primer containing the first sequence, the third primer being tagged with a detectable label; (c) a first oligonucleotide complementary to the single-stranded ends generated in the nucleic acid upon digestion of the nucleic acid with the restriction enzyme corresponding to the polymorphic restriction site, the oligonucleotide being tagged with the first member of a first specific binding pair; (d) the second member of the first specific binding pair, immobilized on a first solid support; and (e) a second oligonucleotide complementary to a second sequence in the strand of the nucleic acid corresponding to the first primer, the sequence being between the polymorphic restriction site and either the sequence corresponding to or complementary to the second primer or the sequence corresponding to or complementary to the first primer, the second oligonucleotide being immobilized on a second solid support.

In a thirty-seventh aspect, the invention features a method for detecting the presence or absence of a polymorphic restriction site in a nucleic acid, involving the steps of: (a) amplifying the nucleic acid by PCR using a first and a second primer flanking the polymorphic restriction site, whereby the resultant PCR product is of a defined size readily resolved by gel electrophoresis; (b) digesting the PCR product of step (a) with the restriction endonuclease corresponding to the polymorphic restriction site, the digestion products being differentially sized; (c) separating the reaction products of step (b) by gel electrophoresis; and (d) detecting the separated reaction products, the presence of only uncleaved products being an indication of a homozygote lacking the polymorphic restriction site, the presence of only cleaved products being an indication of a homozygote containing the polymorphic restriction site, and the presence of both cleaved and uncleaved products being an indication of a heterozygote. In a preferred embodiment, one or both of the first and second primers are tagged with a detectable label. In another preferred embodiment, the PCR product is 100–1000 base pairs in length.

In a thirty-eighth aspect, the invention features a kit for detecting the presence or absence of a polymorphic restriction site in a nucleic acid, the kit containing: a first and a second primer flanking the polymorphic restriction site and capable of generating a PCR product of a defined size that is readily resolved by gel electrophoresis. In a preferred embodiment, the first and/or the second primers are detectably labeled. In another preferred embodiment, the PCR product generated is between 100 and 1000 base pairs in length.

In a thirty-ninth aspect, the invention features a method for identifying a polymorphic restriction site in a nucleic acid, involving the steps of: (a) digesting DNA isolated from a first sample with a first restriction endonuclease; (b) ligating to each of the ends of the reaction products of step (a) a first adaptor; (c) digesting the products of step (b) with a second restriction endonuclease; (d) ligating to each of the ends of the reaction products generated in step (c) a second adaptor; (e) amplifying the reaction products of step (d) by PCR using a first primer complementary to the first adaptor and a second primer complementary to the second adaptor, the second primer being tagged with a first member of a specific binding pair (preferably, biotin); (f) in a separate set of reactions, digesting DNA isolated from a second sample with the first restriction endonuclease; (g) ligating to each of the ends of the reaction products of step (f) a third adaptor; (h) digesting the products of step (g) with the second restriction endonuclease; (i) denaturing the products of step (e) and the products of step (h); (j) combining the denatured products of step (i) under conditions allowing hybridization; (k) contacting the hybridization products of step (j) with the second member of the specific binding pair (preferably, avidin), the second member being immobilized on a solid support; (l) recovering the hybridization products captured on the solid support; and (m) amplifying the products obtained in step (l) by PCR using a primer complementary to the third adaptor, an amplified product being an indication of a polymorphic restriction site corresponding to the second restriction endonuclease.

In a fortieth aspect, the invention features a kit for identifying a polymorphic restriction site in a nucleic acid, the kit containing: (a) a first DNA adaptor, a second DNA adaptor, and a third DNA adaptor, the first and third DNA adaptors having regions complementary to the ends generated by a first restriction endonuclease ends but differing in overall sequence and the second DNA adaptor having a region complementary to the ends generated by a second restriction endonuclease, the second restriction endonuclease site corresponding to the polymorphic restriction site; and (b) a first primer, a second primer, and a third primer, the first primer being complementary to the first DNA adaptor, the second primer being complementary to the second DNA adaptor and being tagged with a first member of a specific binding pair, and the third primer being complementary to the third DNA adaptor. This kit may further contain the second member of the specific binding pair immobilized on a solid support.

In a forty-first aspect, the invention features a method for detecting the presence or absence of a polymorphic restriction site in a nucleic acid. In this method the nucleic acid is amplified by PCR using a first and a second primer flanking the polymorphic restriction site. The first primer is tagged with a detectable label, and the amplifying generates a PCR product containing a first strand tagged with the detectable label and an unlabeled second strand.

The PCR product is then digested with a restriction endonuclease corresponding to the polymorphic restriction site to generate a digestion product, which is denatured to generate a denatured product The denatured product is contacted with a first probe, which contains a sequence that hybridizes to a first sequence in the first strand that is between the polymorphic restriction site and the sequence in the first strand that is complementary to the second primer. The first probe is also immobilized on a first binding element.

The first binding element is monitored for the presence of the detectable label, and detection of the detectable label on the first binding element indicates the absence of the polymorphic restriction site in the nucleic acid, and a failure to detect the detectable label on the first binding element indicates the presence of the polymorphic restriction site in the nucleic acid. The first binding element is a region on a solid support, such as a glass plate or a microchip.

This method can also include contacting the denatured product with a second, a third, or a fourth probe. The second probe, which is immobilized on a second binding element, contains a sequence that hybridizes to a second sequence in the first strand that is between the polymorphic restriction site and the sequence in the first strand that corresponds to the first primer. The third probe, which is immobilized on a third binding element, contains a sequence that hybridizes to a third sequence in the second strand that is between the polymorphic restriction site and the sequence in the second strand corresponding to the second primer. The fourth probe, which is immobilized on a fourth binding element, contains a sequence that hybridizes to a fourth sequence in the second strand that is between the polymorphic restriction site and the sequence in the second strand that is complementary to the first primer. In this method, the second, third, or fourth binding element can be monitored for the presence of the detectable label. The first, second, third, and fourth binding elements can each be distinct regions on a solid support, such as a glass plate or a microchip.

In a forty-second aspect, the invention features a method for detecting the presence or absence of a polymorphic restriction site in a nucleic acid. In this method the nucleic acid is amplified by PCR using a first and a second primer flanking the polymorphic restriction site. The first primer is tagged with a first detectable label and the second primer is tagged with a second detectable label. The amplifying generates a PCR product containing a first strand tagged with the first detectable label and a second strand tagged with the second detectable label. The first and second detectable labels can be identical or distinct.

The PCR product is treated with a restriction endonuclease corresponding to the polymorphic restriction site to generate a digestion product, which is denatured to generate a denatured product. The denatured product is contacted with a first and a second probe. The first probe, which is immobilized on a first binding element, contains a sequence that hybridizes to a first sequence in the first strand that is between the polymorphic restriction site and the sequence in the first strand that is complementary to the second primer. The second probe, which is immobilized on a second binding element, contains a sequence that hybridizes to a second sequence in the second strand that is between the polymorphic restriction site and the sequence in the second strand that is complementary to the first primer. The first and second binding elements can each be distinct regions on a solid support, such as a glass plate or a microchip.

The first binding element is monitored for the presence of the first detectable label and the second binding element is monitored for the presence of the second detectable label. Detection of the first detectable label on the first binding element and detection of the second detectable label on the second binding element indicates the absence of the polymorphic restriction site in the nucleic acid, and a failure to detect the first detectable label on the first binding element and a failure to detect the second detectable label on the second binding element indicates the presence of the polymorphic restriction site in the nucleic acid.

This method can also include contacting the denatured product with a third or a fourth probe. The third probe, which is immobilized on a third binding element, contains a sequence that hybridizes to a third sequence in the first strand that is between the polymorphic restriction site and the sequence in the first strand corresponding to the first primer. The fourth probe, which is immobilized on a fourth binding element, contains a sequence that hybridizes to a fourth sequence in the second strand that is between the polymorphic restriction site and the sequence in the second strand corresponding to the second primer. The third or fourth binding element can be monitored for the presence of the first or second detectable label. The first, second, third, and fourth binding elements can be each distinct regions on a solid support, such as a glass plate or a microchip.

In a forty-third aspect, the invention features a method for detecting the presence or absence of a polymorphic restriction site in a nucleic acid. In this method, the nucleic acid is amplified by PCR using a first and a second primer flanking the polymorphic restriction site. The amplifying generates a PCR product containing a first strand containing a sequence corresponding to the first primer and a second strand containing a sequence corresponding to the second primer.

The PCR product is treated with a restriction endonuclease corresponding to the polymorphic restriction site to generate a digestion product, which is denatured to generate a denatured product. The denatured product is contacted with an oligonucleotide to generate a first reaction product. The oligonucleotide contains a 3' portion that hybridizes to a first region in the first strand that flanks the polymorphic restriction site on the side of the polymorphic restriction site containing a sequence corresponding to the first primer. The oligonucleotide is blocked so that it cannot serve as a primer for DNA polymerase. In addition, the oligonucleotide contains a 5' portion that does not hybridize to a second region in the first strand that flanks the polymorphic restriction site on the side of the polymorphic restriction site containing a sequence that is complementary to the second primer.

The first reaction product is treated with a DNA polymerase to extend the unblocked, primed 3' end to generate a second reaction product, which is amplified by PCR using the first primer, tagged with a first detectable label, and a third primer that hybridizes to a sequence that is complementary to the 5' portion of the oligonucleotide, to generate a second PCR product. The third primer is tagged with a second detectable label. The first and the second detectable labels in this method can be identical or distinct.

The second PCR product is denatured to generate a second denatured product, which is contacted with a first and a second probe. The first probe, which is immobilized on a first binding element, contains a sequence that hybridizes to a first sequence in the second strand that is between the polymorphic restriction site and the sequence in the second strand that is complementary to the first primer The second probe, which is immobilized on a second binding element, contains a sequence that hybridizes to a second sequence in the first strand that is between the polymorphic restriction site and the sequence in the first strand that is complementary to the second primer. The first and second binding elements can each be distinct regions on a solid support, such as a glass support or a microchip.

The first binding element is monitored for the presence of the second detectable label and the second binding element is monitored for the presence of the first detectable label. Detection of the second detectable label on the first binding element and detection of the first detectable label on the second binding element indicates a heterozygote, detection of the second detectable label on the first binding element and a failure to detect the first detectable label on the second binding element indicates a homozygote containing the polymorphic restriction site, and detection of the first detectable label on the second binding element and a failure to detect the second detectable label on the first binding element indicates a homozygote lacking the polymorphic restriction site.

This method can also include contacting the second denatured product with a third or a fourth probe. The third probe, which is immobilized on a third binding element, contains a sequence that hybridizes to a third sequence in the first strand that is between the polymorphic restriction site and the sequence in the first strand corresponding to the first primer The fourth probe, which is immobilized on a fourth binding element, contains a sequence that hybridizes to a fourth sequence in the second strand that is between the polymorphic restriction site and the sequence in the second strand corresponding to the second primer. The third or fourth binding element can be monitored for the presence of the first or second detectable label. The first, second, third, and fourth binding elements can each be distinct regions on a solid support, such as a glass plate or a microchip.

In a forty-fourth aspect, the invention features a kit for detecting the presence or absence of a polymorphic restriction site in a nucleic acid. The kit can contain one or more sets of a first and a second primer flanking the polymorphic restriction site. The first primer is tagged with a detectable label, so that amplifying the nucleic acid by PCR with the first and second primers generates a PCR product containing a first strand tagged with the detectable label and a second strand. The kit also can include one or more first probes, each of which containing a sequence that hybridizes to a first sequence in the first strand that is between the polymorphic restriction site and the sequence in the first strand that is complementary to the second primer. Each of the first probes is immobilized on a first binding element.

This kit can also contain one or more sets of a second, third, or fourth probe. Each of the second probes, which is immobilized on a second binding element, contains a sequence that hybridizes to a second sequence in the first strand that is between the polymorphic restriction site and the sequence in the first strand that corresponds to the first primer. Each of the third probes, which is immobilized on a third binding element, contains a sequence that hybridizes to a third sequence in the second strand that is between the polymorphic restriction site and the sequence in the second strand corresponding to the second primer. Each of the fourth probes, which is immobilized on a fourth binding element, contains a sequence that hybridizes to a fourth sequence in the second strand that is between the polymorphic restriction site and the sequence in the second strand that is complementary to the first primer.

The first binding element in this kit can be a region on a solid support, such as a glass plate or a microchip. In addition, in this kit, the first, second, third, and fourth binding elements can each be distinct regions on a solid support, such as a glass plate or a microchip.

One or more second primers in this kit can each contain a second detectable label. In addition, the kit can further contain a second probe, which is immobilized on a second binding element, and contains a sequence that hybridizes to a second sequence in the second strand that is between the polymorphic restriction site and the sequence in the second strand that is complementary to the first primer.

The kit can also contain one or more sets of a third or a fourth probe. Each of the third probes, which are immobilized on a third binding element, contain a sequence that hybridizes to a third sequence in the first strand that is between the polymorphic restriction site and the sequence in the first strand corresponding to the first primer. Each of the fourth probes, which are immobilized on a fourth binding element, contain a sequence that hybridizes to a fourth sequence in the second strand that is between the polymorphic restriction site and the sequence in the second strand corresponding to the second primer.

The kit can further contain one or more second probes, which are immobilized on a second binding element, that each contain a sequence that hybridizes to a second sequence in the first strand that is between the polymorphic restriction site and the sequence in the first strand that corresponds to the first primer.

In a forty-fifth aspect, the invention features a kit for detecting the presence or absence of a polymorphic restriction site in a nucleic acid. This kit can contain one or more sets of a first and a second PCR primer flanking the polymorphic restriction site. The first primer can be tagged with a first detectable label, so that amplifying the nucleic acid by PCR using the first and second primers generates a PCR product containing a first strand tagged with the first detectable label and a second strand. Alternatively, the first primer can be unlabeled.

This kit can also include one or more oligonucleotides containing a 3' portion that hybridizes to a first region in the first strand that flanks the polymorphic restriction site on the side of the polymorphic restriction site containing a sequence corresponding to the first primer. The oligonucleotide is blocked so that it cannot serve as a primer for DNA polymerase. In addition, the oligonucleotide contains a 5' portion that does not hybridize to a second region in the first strand that flanks the polymorphic restriction site on the side of the polymorphic restriction site containing a sequence that is complementary to the second primer.

This kit can also include one or more third primers, each of which that hybridizes to a sequence that is complementary to the 5' portion of the oligonucleotide The third primer can be tagged with a second detectable label.

Also included in this kit are one or more sets of a first and a second probe. Each of the first probes, which are immobilized on a first solid support, contain a sequence that hybridizes to a first sequence in the second strand that is between the polymorphic restriction site and the sequence in the second strand that is complementary to the first primer. Each of the second probes, which are immobilized on a second solid support, contain a sequence that hybridizes to a second sequence in the first strand that is between the polymorphic restriction site and the sequence in the first strand that is complementary to the second primer.

The first and the second detectable labels in this kit can be distinct or identical. In addition, the first and second binding elements can each be distinct regions on a solid support, such as a glass support or a microchip.

This kit can further contain one or more sets of a third or a fourth probe. Each of the third probes, which are immobilized on a third binding element, contain a sequence that hybridizes to a third sequence in the first strand that is between the polymorphic restriction site and the sequence in the first strand corresponding to the first primer. Each of the fourth probes, which are immobilized on a fourth binding element, contain a sequence that hybridizes to a fourth sequence in the second strand that is between the polymorphic restriction site and the sequence in the second strand corresponding to the second primer.

The one or more sets of the first, second, third, and fourth binding elements in this kit can each be distinct regions on a solid support, such as a glass plate or a microchip.

In a preferred embodiment of various of the above aspects, multiple polymorphic restriction sites are detected by the method or kit. In preferred embodiments of various of the above aspects, the detectable label is selected from the group consisting of digoxigenin, fluorescent labels (e.g., fluorescein and rhodamine), enzymes (e.g., horseradish peroxidase and alkaline phosphatase), biotin (which can be detected by anti-biotin specific antibodies or enzyme-conjugated avidin derivatives), radioactive labels (e.g., $^{32}P$ and $^{125}I$), calorimetric reagents, and chemiluminescent reagents.

In other preferred embodiments of various of the above aspects, the specific binding pairs are selected from the group consisting of avidin-biotin, streptavidin-biotin, hybridizing nucleic acid pairs, interacting protein pairs, antibody-antigen pairs, reagents containing chemically reactive groups (e.g., reactive amino groups), and nucleic acid sequence-nucleic acid binding protein pairs. In related preferred embodiments of various of the above aspects, the solid supports used in the methods of the invention are selected from the group consisting of agarose, acrylamide, and polystyrene beads; polystyrene microtiter plates (for use in, e.g., ELISA); silicon, gold, or glass chips (e.g., microchips), slides, or plates; and nylon and nitrocellulose membranes (for use in, e.g., dot or slot blot assays).

The term "heterozygote," as used herein, refers to an individual with different alleles at corresponding loci on homologous chromosomes. Accordingly, the term "heterozygous," as used herein, describes an individual or strain having different allelic genes at one or more paired loci on homologous chromosomes.

The term "homozygote," as used herein, refers to an individual with the same allele at corresponding loci on homologous chromosomes. Accordingly, the term "homozygous," as used herein, describes an individual or a strain having identical allelic genes at one or more paired loci on homologous chromosomes.

The term "corresponding" as used herein to describe a nucleic acid strand, e.g., a nucleic acid strand corresponding to a particular PCR primer, is meant to indicate that the strand contains the sequence of the particular PCR primer. When used to compare a polymorphic restriction site to a restriction endonuclease site, the term again indicates that the two sequences are identical.

An advantage of certain detection methods of the present invention over many other methods used to detect genetic polymorphisms is that gel electrophoresis is not required in the analysis. Thus, the methods of the present invention are readily adaptable for automation, allowing large numbers of samples to be processed in relatively short periods of time, at lower costs. In certain of the embodiments, detection of an array of samples is carried out simultaneously on a solid support, such as a glass slide or a microchip, further reducing processing time and cost. Detection of signals on arrays can be carried out quantitatively or qualitatively. In addition, in several variations of the methods of the invention (see, e.g., Examples III and IV below), internal controls are provided, thus controlling for variability detected by different practitioners. Furthermore, in several of the variations of the methods of the invention (see Examples III–VIII and XII–XIV below), an oligonucleotide probe hybridizing to a sequence in the PCR product internal to the primers is used to purify the products, thus allowing a reduction in background problems associated with PCR amplification.

Those detection methods of the invention utilizing gel electrophoresis are also advantageous because they provide a rapid and inexpensive approach to the identification of large numbers of PCR-based genetic and RFLP markers.

The method of the invention useful for cloning genetic polymorphisms also represents an improvement over current methods. Because the process of selecting out a tagged (e.g., biotinylated) DNA having a polymorphism involves a specific hybridization step, candidate DNA from any source may be utilized. For example, DNA from random clones, CDNA libraries, YAC libraries, or any other DNA collection may be screened; pure preparations of genomic DNAs are not required. Moreover, like other methods of the invention, this cloning procedure is rapid and inexpensive.

All methods of the invention are useful in clinical diagnostic testing, genomic mapping, positional cloning of genes defined by mutation (such as those that cause inherited disease in humans or resistance to pathogens in crop plants), DNA fingerprinting (e.g., for forensic analysis and paternity testing), crop and livestock breeding programs, and other related applications.

In one particular example, the detection methods of the invention are useful for bacterial typing utilizing known conserved polymorphic sequences diagnostic of the bacterium. In one application, this approach is useful for distinguishing one bacterium from another (e.g., for the identification of Salmonella in a food sample); polymorphism-containing sequences preferred for this approach include those present in conserved ribosomal RNA genes. In another application, this approach is useful for screening bacteria (e.g., clinical isolates) for antibiotic resistance; in this case, known polymorphic restriction sites within the antibiotic resistance marker are utilized. The instant methods of bacterial typing decrease false positive results frequently obtained using current PCR-based techniques.

DETAILED DESCRIPTION

The drawings are first described.

Drawings

FIG. 1 is a schematic of a RFLP detection method involving the use of a first PCR primer tagged with a detectable label (x) and a second PCR primer tagged with the first member of a specific binding pair (y). After amplification by PCR, the products are digested with the restriction endonuclease (R) corresponding to the polymorphic restriction site, contacted with the second member of the specific binding pair immobilized on a solid support, and the level of the detectable label (x) bound to the solid support is determined.

FIG. 2 is a schematic of a RFLP detection method involving the use of a first PCR primer tagged with a first detectable label (x) and a second PCR primer tagged with the first member of a specific binding pair (y). After amplification by PCR, the products are digested with the restriction endonuclease (R) corresponding to the polymorphic restriction site, and an oligonucleotide tagged with a second detectable label (Z) is annealed and ligated to the single-stranded ends generated in the digestion. The reaction is then contacted with the second member of the specific binding pair bound to a solid support, and the levels of the first and second detectable labels (X and Z) bound to the solid support are determined.

FIG. 3 is a schematic of a RFLP detection method involving the use of a first PCR primer tagged with a detectable label (P1) and a second unlabeled PCR primer (P2). After amplification by PCR, half of the reaction (or one of the identical reactions if carried out in duplicate) is digested with the restriction endonuclease (R) corresponding to the polymorphic restriction site. Both digested and undigested reactions are then denatured and contacted with an oligonucleotide tagged with the first member of a specific binding pair, the oligonucleotide being complementary to the P1 strand and located to the right of the restriction site (R) near to, but not overlapping, primer P2. The reactions are then contacted with the second member of the specific binding pair immobilized on a solid support, and the levels of P1 in digested versus undigested reactions are compared.

FIG. 4 is a schematic of a RFLP detection method involving the use of a first PCR primer tagged with a first detectable label (P1) and a second PCR primer tagged with a second detectable label (P2). After amplification by PCR, the products are digested with the restriction endonuclease (R) corresponding to the polymorphic restriction site, denatured, and contacted with a first oligonucleotide complementary to the P1 strand and located to the right of the restriction site (R) near to, but not overlapping primer P2, and a second oligonucleotide complementary to the P2 strand and located to the right of the restriction site (R) near to, but not overlapping the sequence complementary to primer P2. Both the first and second oligonucleotides are tagged with the first member of a specific binding pair (y). The reactions are then contacted with the second member of the specific binding pair immobilized on a solid support, and the ratio of P1 to P2 bound to the solid support is determined.

FIG. 5 is a schematic of a RFLP detection method involving the use of a first PCR primer tagged with a detectable label (x) and a second PCR primer tagged with the first member of a first specific binding pair (y). After amplification by PCR, the products are digested with the restriction enzyme (R) corresponding to the polymorphic restriction site, and are contacted with the second member of the first specific binding pair immobilized on a first solid support. The filtrate is then bound to a solid support with the anchor sequence (or contacted with an oligonucleotide complementary to the X strand between the restriction site (R) and the label (x), the oligonucleotide being tagged with the first member of a second specific binding pair, and then contacted with the second member of the second specific binding pair immobilized on a second solid support), and the levels of the detectable label bound to the first solid support and the anchor sequence (or second solid support) are determined.

FIG. 6 is a schematic of a RFLP detection method involving the use of a first unlabeled PCR primer and a second PCR primer tagged with a detectable label (x). After amplification by PCR, the products are digested with the restriction enzyme (R) corresponding to the polymorphic restriction site, and contacted with an oligonucleotide complementary to the single-stranded ends generated in the digestion, the oligonucleotide being tagged with the first member of a specific binding pair. The products are then contacted with the second member of the first specific binding pair, bound to a first solid support. The filtrate is then bound to a solid support with the anchor sequence (or contacted with an oligonucleotide complementary to the X strand, the oligonucleotide being tagged with the first member of a second specific binding pair, and then contacted with the second member of the second specific binding pair immobilized on a second solid support), and the levels of the detectable label bound to the first solid support and the anchor sequence (or second solid support) are determined.

FIG. 7 is a schematic of a RFLP detection method involving the use of PCR primers flanking the polymorphic restriction site (the "Alu I" site). Following PCR amplification, the reaction products are digested with the restriction endonuclease corresponding to the polymorphic restriction site (Alu I), and the fragments are run on an agarose gel. The separated fragments are detected as an indication of the presence or absence of the polymorphic marker.

FIG. 9A, 9B, 9C, 9D & 9E is a schematic of a method for cloning polymorphic restriction fragments.

METHODS FOR GENERATING AND DETECTING GENETIC POLYMORPHISMS

Figure 1:
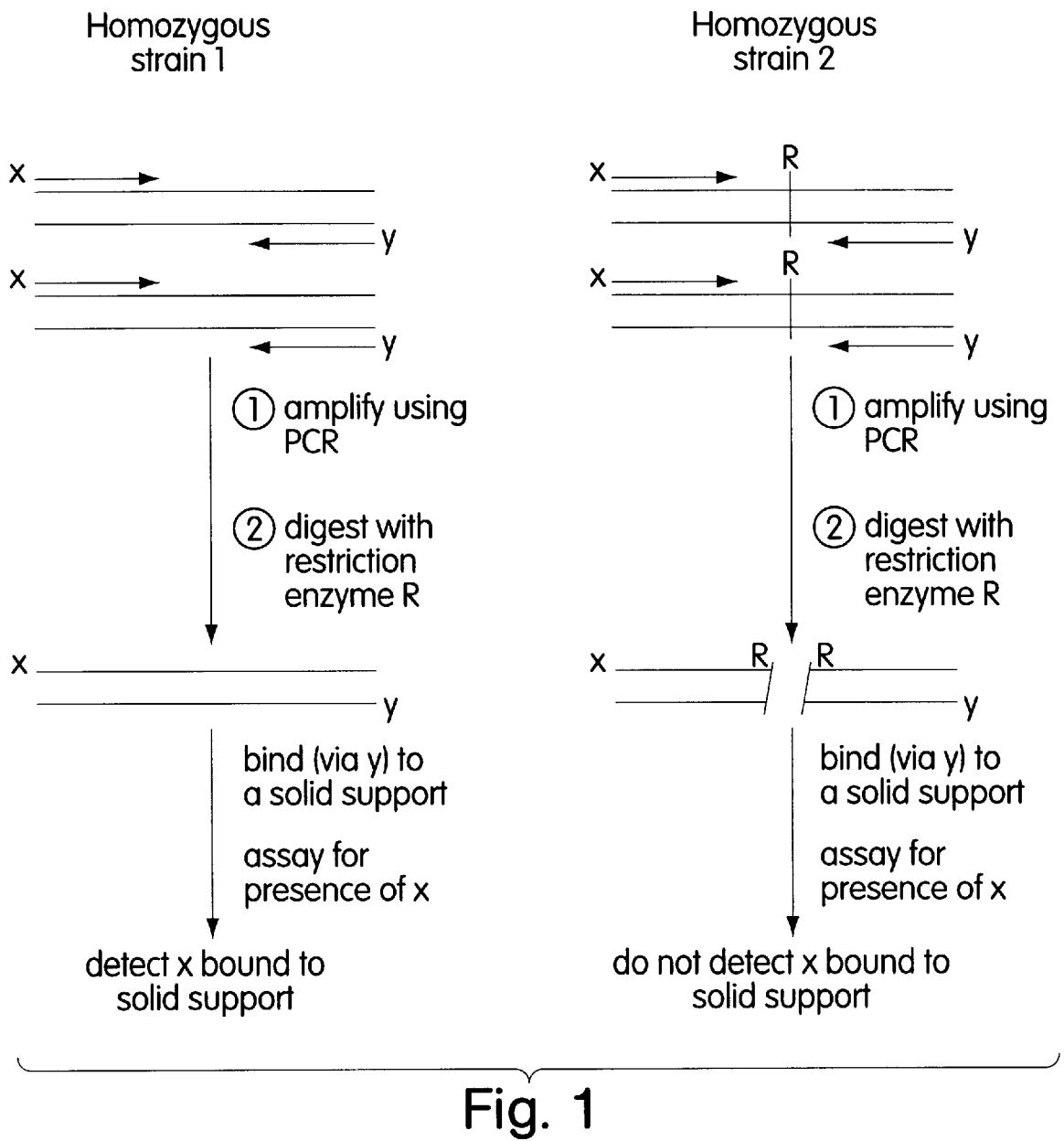

The present invention provides several methods for detecting Cleaved Amplified Polymorphic Sequences (CAPS; Konieczny et al., The Plant Journal 4(2):403–410, 1993). In the CAPS method, a nucleic acid containing a polymorphic restriction site is amplified using primers flanking the restriction site. The resulting PCR product is digested with the restriction endonuclease corresponding to the polymorphic restriction site, and the digested products are analyzed by gel electrophoresis.

The detection methods of the present invention vary greatly from one another in detail, however they share three central features: (1) the nucleic acid containing the polymorphic restriction site is amplified by PCR using differently labeled primers flanking the polymorphic restriction site, (2) the resulting PCR product is digested with the restriction endonuclease corresponding to the polymorphic restriction site (which will cleave the DNA of some individuals but not cleave the DNA of others, depending on the presence of the polymorphism), and (3) the resulting digestion products are analyzed by detection of the labels they contain, and/or labels attached to oligonucleotides complementary to the digestion products, in order to determine the identity of the polymorphic restriction site. The methods of the invention allow rapid and efficient analyses of a large number of samples.

The nucleic acid sample containing the polymorphic restriction site being analyzed can be obtained from any source, e.g., a tissue homogenate, blood, amniotic fluid, chorionic villus samples, and a bacterial culture; and can be obtained from these sources using standard methods. Only a minute quantity of nucleic acid is required, and can be DNA or RNA (in the case of RNA, a reverse transcription step is required before the PCR step) The PCR methods used in the methods of the present invention are carried out using standard methods (see, e.g., Ausubel et al., Current Protocols in Molecular Biology, John Wiley and Sons, New York, 1989; Erlich, PCR Technology, Stockton Press, New York, 1989; Innis et al., PCR Protocols: A Guide to Methods and Applications, Academic Press, Harcourt Brace Javanovich, New York, 1990; Sambrook et al., Molecular Cloning: A Laboratory Manual, Cold Spring Harbor Laboratory Press, Cold Spring Harbor, N.Y., 1989). Restriction enzyme digestion is also carried out by standard methods using any of a number of available restriction endonucleases (see, e.g., Ausubel et al., supra; New England Biolabs, Beverly, Mass.).

The primers and oligonucleotides used in the methods of the present invention are preferably DNA, and can be synthesized using standard techniques and, when appropriate, detectably labeled using standard methods (Ausubel et al., supra). Detectable labels that can be used to tag the primers and oligonucleotides used in the methods of the invention include, but are not limited to, digoxigenin, fluorescent labels (e.g., fluorescein and rhodamine), enzymes (e.g., horseradish peroxidase and alkaline phosphatase), biotin (which can be detected by anti-biotin specific antibodies or enzyme-conjugated avidin derivatives), radioactive labels (e.g., $^{32}P$ and $^{125}I$), calorimetric reagents, and chemiluminescent reagents. The labels used in the methods of the invention are detected using standard methods.

The specific binding pairs useful in the methods of the invention include, but are not limited to, avidin:biotin, streptavidin-biotin, hybridizing nucleic acid pairs, interacting protein pairs, antibody-antigen pairs, reagents containing chemically reactive groups (e.g., reactive amino groups), and nucleic acid sequence-nucleic acid binding protein pairs.

The solid supports useful in the methods of the invention include, but are not limited to, agarose, acrylamide, and polystyrene beads; polystyrene microtiter plates (for use in, e.g. ELISA); and nylon and nitrocellulose membranes (for use in, e.g., dot or slot blot assays).

Some methods of the invention employ solid supports containing arrays of nucleic acid probes. In these cases, solid supports made of materials such as glass (e.g., glass plates), silicon or silicon-glass (e.g., microchips), or gold (e.g., gold plates) can be used. Methods for attaching nucleic acid probes to precise regions on such solid surfaces, e.g., photolithographic methods, are well known in the art, and can be used to make solid supports for use in the invention. (For example, see, Schena et al., Science 270:467–470, 1995; Kozal et al., Nature Medicine 2(7):753–759, 1996; Cheng et al., Nucleic Acids Research 24(2):380–385, 1996; Lipshutz et al., BioTechniques 19(3):442–447, 1995; Pease et al., Proc. Natl. Acad. Sci. USA 91:5022–5026, 1994; Fodor et al., Nature 364:555–556, 1993; Pirrung et al., U.S. Pat. No. 5,143,854; and Fodor et al., WO 92/10092.)

The methods of the invention can be facilitated by the use of kits which contain the reagents required for carrying out the assays. The kits can contain reagents for carrying out the analysis of a single polymorphic restriction site (for use in, e.g., diagnostic methods) or multiple polymorphic restriction sites (for use in, e.g., genomic mapping). When multiple samples are analyzed, multiple sets of the appropriate primers and oligonucleotides are provided in the kit. In addition to the primers and oligonucleotides required for carrying out the various methods, the kits may contain the enzymes used in the methods, and the reagents for detecting the labels, e.g., the substrates for enzyme labels, etc. The kits can also contain solid substrates for used in carrying out the method of the invention. For example, the kits can contain solid substrates, such as glass plates or silicon or glass microchips, containing arrays of nucleic acid probes.

As discussed above, the invention provides methods and kits for generating and detecting the presence or absence of a polymorphic restriction site in a nucleic acid. Examples I–IX and XII–XIV describe eight variations of the methods of the invention. Example X describes a preferred use for the methods of the invention. Example XI describes a preferred method for cloning polymorphic restriction fragments. The following examples are meant to illustrate, but not limit, the methods of the present invention. Other suitable modifications and adaptations of the variety of conditions and parameters of molecular biology which are obvious to those skilled in the art are within the spirit and scope of the present invention.

EXAMPLES

Example I

In this method, the nucleic acid containing the polymorphism is amplified by PCR using a first and a second primer flanking the polymorphic restriction site, the first primer being tagged with the first member of a specific binding pair, the second primer being tagged with a detectable label. The resulting PCR product is digested with the restriction endonuclease corresponding to the polymorphic restriction site and the digested products are contacted with the second member of the specific binding pair, immobilized on a solid support The level of the detectable label bound to the solid support is then measured. The presence of the detectable label bound to the solid support is an indication of the absence of the polymorphic restriction site in the nucleic acid, while the absence of the detectable label bound to the solid support is an indication of the presence of the polymorphic restriction site in the nucleic acid. An embodiment of this method is shown in FIG. 1.

Example II

Figure 2:
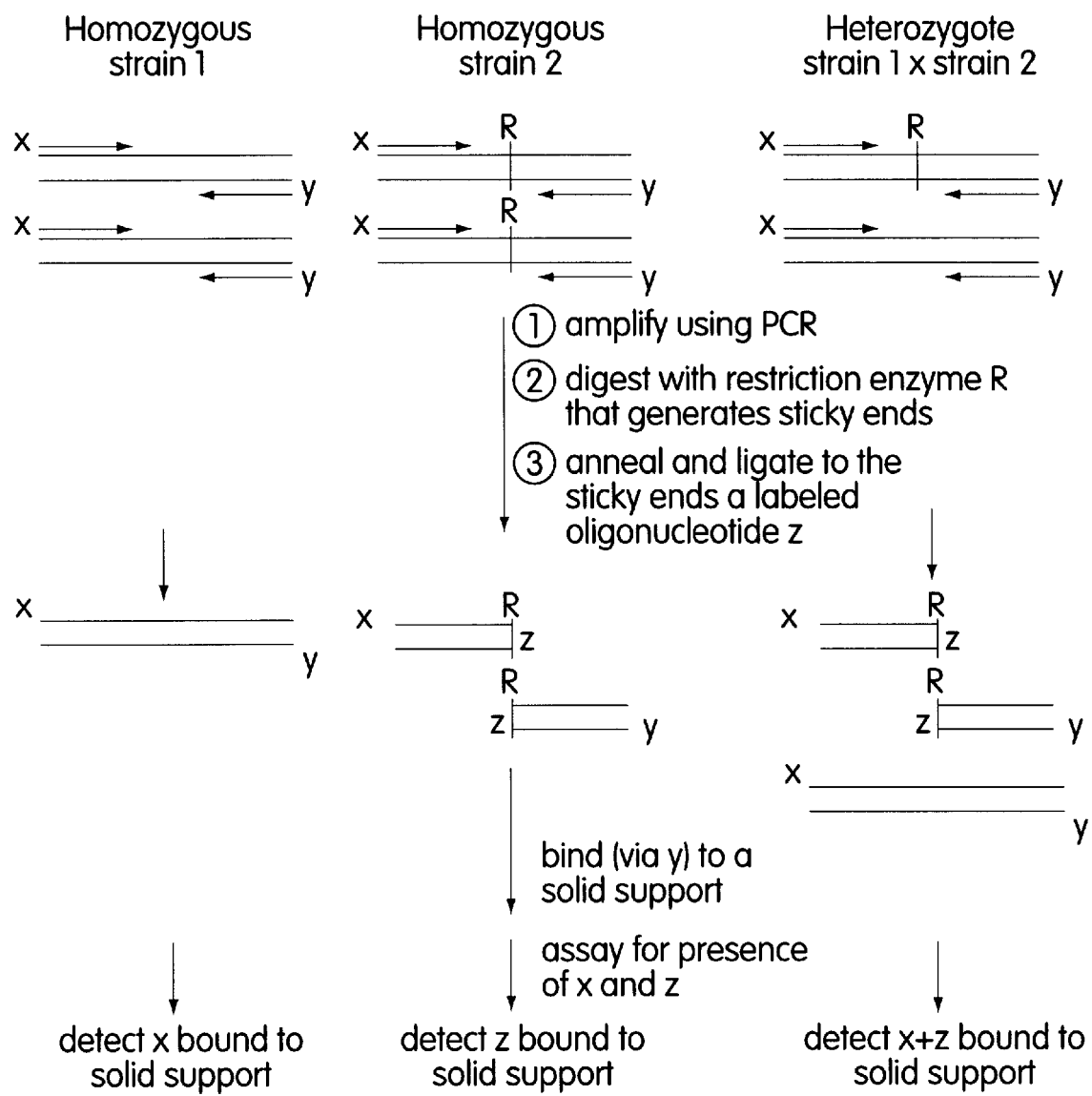

This method is identical to that described in Example I, with the added step of annealing and ligating to the single-stranded ends generated in the digestion reaction, an oligonucleotide tagged with a second detectable label. After applying the reaction to the second member of the specific binding pair, the levels of both the first and the second detectable labels bound to the solid support are determined. The presence of only the first detectable label bound to the solid support is an indication of a homozygote lacking the polymorphic restriction site, the presence of only the second detectable label bound to the solid support is an indication of a homozygote containing the polymorphic restriction site, and the presence of both the first and the second detectable labels bound to the solid support is an indication of a heterozygote. An embodiment of this method is shown in FIG. 2.

Figure 12:
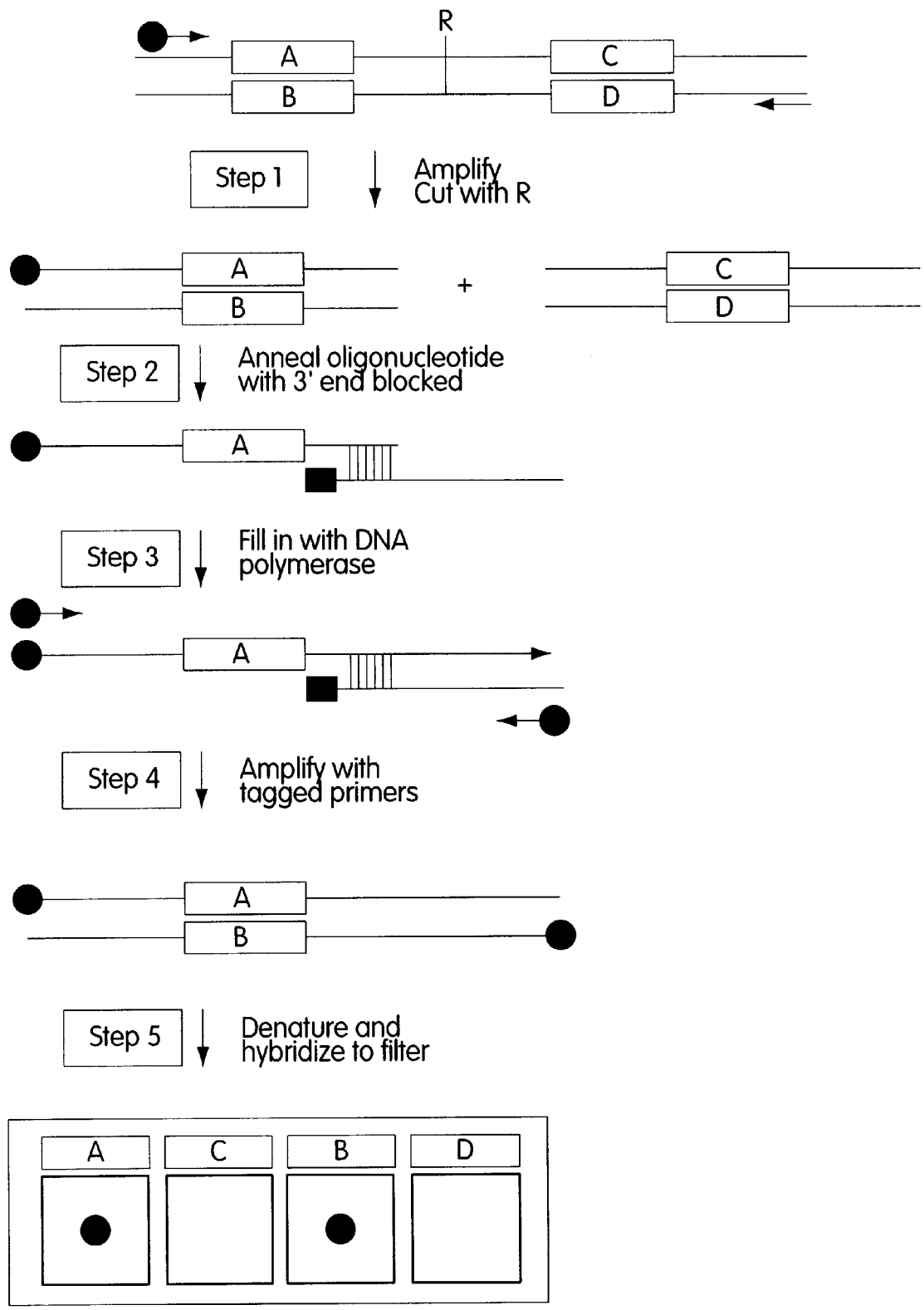
FIG. 12 is a schematic of a method for detecting a cleaved end of a CAPS marker.

In addition to labeling the cleaved ends of the CAPS products by annealing and ligating an oligonucleotide to the sticky ends generated by the cleavage, as is described above, and, e.g., in Examples VI and VIII, the cleaved ends can be labeled by using a method described in further detail below in Example XIV. Briefly, in this method, the denatured product is contacted with an oligonucleotide to generate a first reaction product. The oligonucleotide contains a 3' portion that hybridizes to a first region in the first strand that flanks the polymorphic restriction site on the side of the polymorphic restriction site containing a sequence corresponding to the first primer. The 3' end of the oligonucleotide is blocked by, e.g., a di-deoxynucleotide, so that it cannot serve as a primer for DNA polymerase. The oligonucleotide contains a 5' portion that does not hybridize to a second region in the first strand that flanks the polymorphic restriction site on the side of the polymorphic restriction site containing a sequence that is complementary to the second primer. The use of such an oligonucleotide to label a cleaved end of a CAPS marker is illustrated in FIG. 12. This method can also be applied to the CAPS detection techniques of, for example, Examples VI and VIII.

Example III

In this method, the nucleic acid is amplified using a first and a second primer flanking the polymorphic restriction site, the first primer being tagged with a detectable label, the second primer being unlabeled. A portion of the PCR reaction is digested with the restriction endonuclease corresponding to the polymorphic restriction site, while another portion is left undigested. Both the digested and undigested portions are then denatured, and contacted with an oligonucleotide tagged with the first member of a specific binding pair. The oligonucleotide is complementary to a sequence in the strand of the PCR product containing the detectable label, the sequence being between the polymorphic restriction site and the sequence complementary to the second primer.

Figure 3:
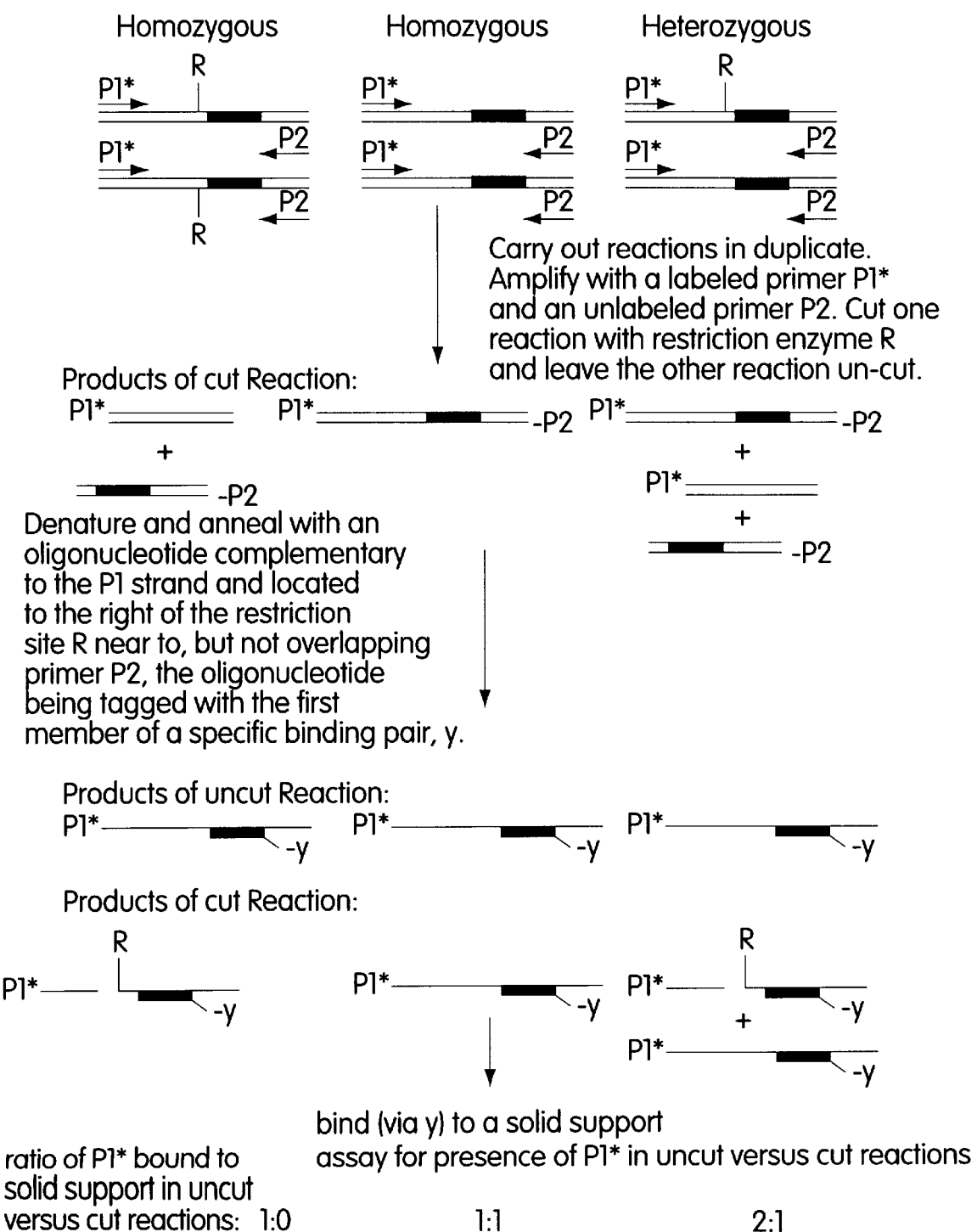

The reaction is then contacted with the second member of the specific binding pair, immobilized on a solid support, and the ratio of the levels of the detectable label bound to the solid support between undigested and digested samples is determined. A ratio of 1:0 between equivalent portions of undigested and digested samples is an indication of a homozygote containing the polymorphic restriction site, a ratio of 1:1 between equivalent portions of undigested and digested samples is an indication of a homozygote lacking the polymorphic restriction site, and a ratio of 2:1 between equivalent portions of undigested and digested samples is an indication of a heterozygote. While the sample volumes used for detection and comparison need not be equivalent, the appropriate calculations must be carried out to account for this adjustment prior to determining the ratio of detectable label in digested and undigested samples. An embodiment of this method is shown in FIG. 3.

Example IV

In this method, the nucleic acid is amplified by PCR using a first primer and a second primer flanking the polymorphic restriction site, the first primer being tagged with a first detectable label, and the second primer being tagged with a second detectable label.

The PCR product is digested with the restriction endonuclease corresponding to the polymorphic restriction site, denatured, and contacting with a first and a second oligonucleotide. The first oligonucleotide is complementary to a first sequence in the strand of the PCR product containing the first detectable label, the first sequence being between the polymorphic restriction site and the sequence corresponding to the first primer The first oligonucleotide is tagged with the first member of a first specific binding pair. The second oligonucleotide is complementary to a second sequence in the strand of the PCR product containing the second detectable label. The second sequence is on the same side of the polymorphic restriction site as the first sequence, and is not contained within, or complementary to, either the first or the second primer. The second oligonucleotide is tagged with the first member of a second specific binding pair.

A first portion of the reaction is then contacted with the second member of the first specific binding pair, immobilized on a first solid support, while a second portion of the reaction is contacted with the second member of the second specific binding pair, immobilized on a second solid support. The ratio of the levels of the first and second detectable labels bound to the first and second solid supports is then determined. A ratio of 1:0 between equivalent amounts of the first and second portions is an indication of a homozygote containing the polymorphic restriction site, a ratio of 1:1 between equivalent amounts of the first and second portions is an indication of a homozygote lacking the polymorphic restriction site, and a ratio of 2:1 between equivalent amounts of the first and second portions is an indication of a heterozygote.

Figure 4:
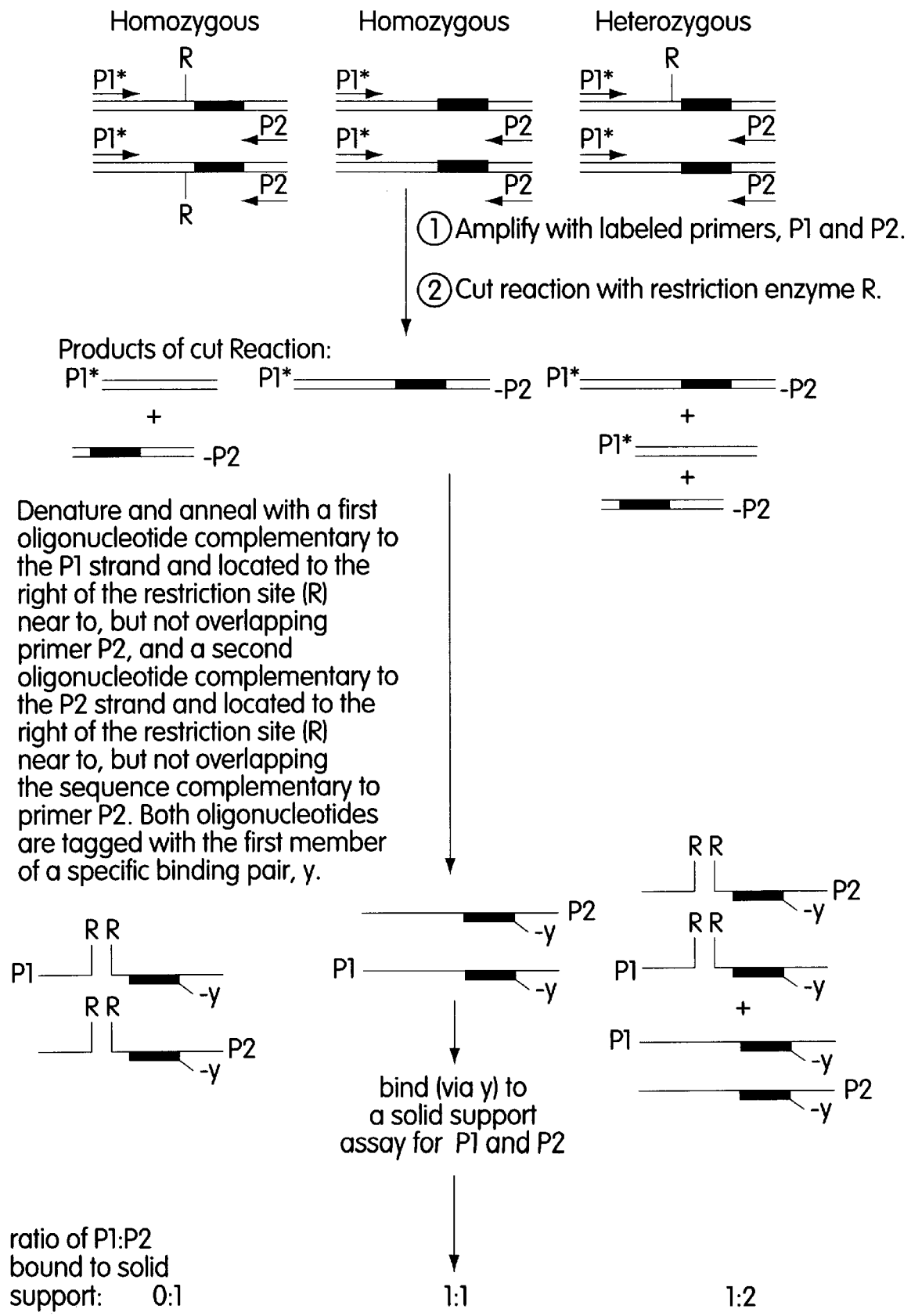

In the case where the first sequence (to which the first oligonucleotide is complementary) in the strand containing the first detectable label is between the polymorphic restriction site and the sequence complementary to the second primer, the ratios differ, as follows. The ratio of the levels of the first and second detectable labels bound to the first and second solid supports is 0:1 between equivalent amounts of the first and second portions in the case of a homozygote containing the polymorphic restriction site The ratio is 1:1 between equivalent amounts of the first and second portions in the case of a homozygote lacking the polymorphic restriction site, and the ratio is 1:2 between equivalent amounts of the first and second portions in the case of a heterozygote An embodiment of this method is shown in FIG. 4.

Example V

In this method, the nucleic acid is amplified by PCR using a first and a second primer flanking the polymorphic restriction site, the first primer being tagged with the first member of a first specific binding pair, the second primer being tagged with a detectable label. The PCR product is digested with the restriction endonuclease corresponding to the polymorphic restriction site, and the reaction is then contacted with the second member of the first specific binding pair, immobilized on a first solid support.

Figure 5:
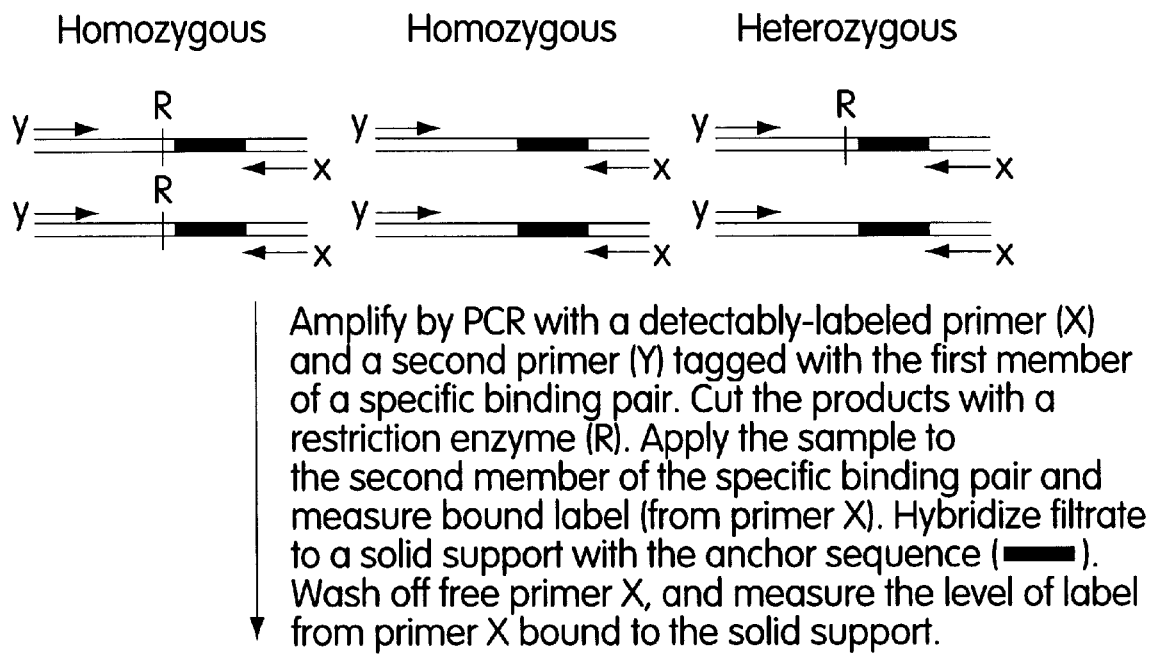
Figure 5:
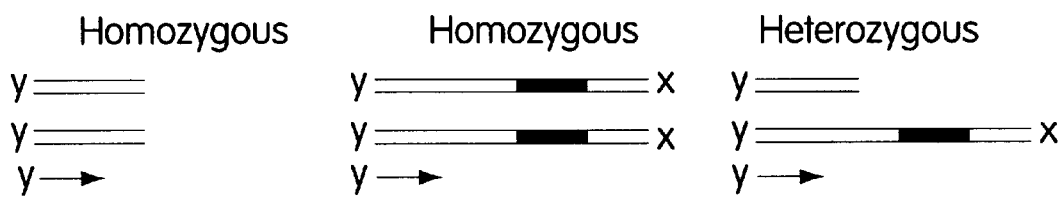
Figure 5:
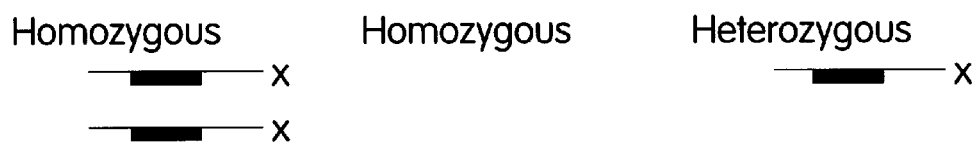

The material not bound to the first solid support is denatured and contacted with an oligonucleotide complementary to a sequence in the strand of the PCR product containing the detectable label. The sequence is between the polymorphic restriction site and the sequence corresponding to the second primer, and the oligonucleotide is tagged with the first member of a second specific binding pair. The reaction is then contacted with the second member of the second specific binding pair, immobilized on a second solid support, and the ratio of the level of the detectable label bound to the first solid support compared to the level of the detectable label bound to the second solid support is determined. A ratio of 0:1 is an indication of a homozygote containing the polymorphic restriction site, a ratio of 1:0 is an indication of a homozygote lacking the polymorphic restriction site, and a ratio of 1:1 is an indication of a heterozygote. These ratios are correct in cases where the total amount of the material not bound to the first solid support is used in the following steps, and should be adjusted accordingly, if a different amount of the material is used. An embodiment of this method is shown in FIG. 5.

Example VI

In this method, the nucleic acid is amplified by PCR using a first and a second primer flanking the polymorphic restriction site, the first primer being tagged with a detectable label, the second primer being unlabeled. The PCR product is digested with the restriction endonuclease corresponding to the polymorphic restriction site, and a first oligonucleotide tagged with the first member of a first specific binding pair is annealed and ligated to the single-stranded ends generated in the digestion reaction. The reaction is then contacted with the second member of the first specific binding pair, immobilized on a first solid support.

Figure 6:
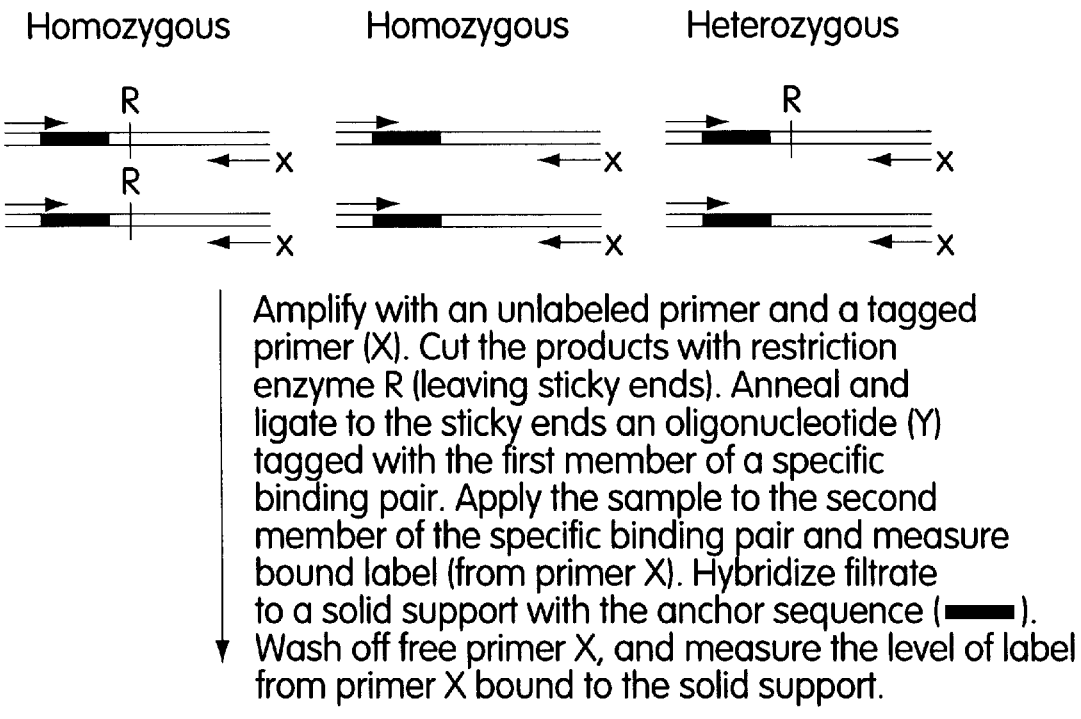
Figure 6:
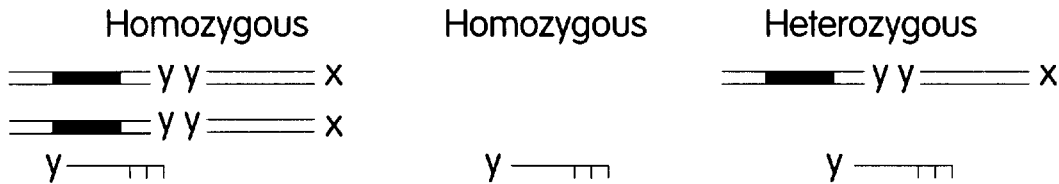
Figure 6:
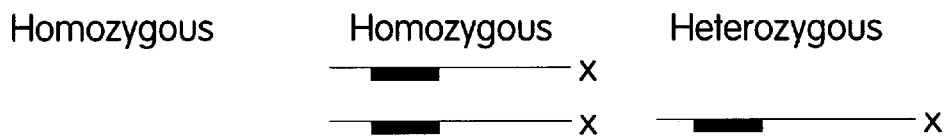

The material not bound to the first solid support is denatured, and contacted with a second oligonucleotide complementary to a sequence in the strand of the PCR product containing the detectable label, the sequence being between the polymorphic restriction site and either the sequence corresponding to the first primer or the sequence complementary to the second primer. The second oligonucleotide is tagged with the first member of a second specific binding pair. The reaction is then contacted with the second member of the second specific binding pair, immobilized on a second solid support, and the ratio of the level of the detectable label bound to the first solid support compared to the level of the detectable label bound to the second solid support is determined. A ratio of 1:0 is an indication of a homozygote containing the polymorphic restriction site, a ratio of 0:1 is an indication of a homozygote lacking the polymorphic restriction site, and a ratio of 1:1 is an indication of a heterozygote. These ratios are correct in cases where the total amount of the material not bound to the first solid support is used in the following steps, and should be adjusted accordingly, if a different amount of the material is used. An embodiment of this method is shown in FIG. 6.

Example VII

In this method, the nucleic acid is amplified by PCR using a first and a second primer flanking the polymorphic restriction site, the first primer being tagged with the first member of a first specific binding pair, the second primer being tagged with a detectable label. The PCR product is digested with the restriction endonuclease corresponding to the polymorphic restriction site, and contacted with the second member of the first specific binding pair, immobilized on a first solid support.

The material not bound to the first solid support is denatured and contacted with an oligonucleotide complementary to a sequence in the strand of the PCR product containing the detectable label. The sequence is between the polymorphic restriction site and the sequence corresponding to the second primer, and the oligonucleotide is immobilized on a second solid support (e.g., a nylon or nitrocellulose membrane).

The ratio of the level of detectable label bound to the first solid support to the level of detectable label bound to the second solid support is then determined. A ratio of 0:1 is an indication of a homozygote containing the polymorphic restriction site, a ratio of 1:0 is an indication of a homozygote lacking the polymorphic restriction site, and a ratio of 1:1 is an indication of a heterozygote. These ratios are correct in cases where the total amount of the material not bound to the first solid support is used in the following steps, and should be adjusted accordingly, if a different amount of the material is used. An embodiment of this method is shown in FIG. 5.

Example VIII

In this method, the nucleic acid is amplified by PCR using a first and a second primer flanking the polymorphic restriction site, the first primer being tagged with a detectable label, the second primer being unlabeled. The PCR product is digested with the restriction endonuclease corresponding to the polymorphic restriction site, and a first oligonucleotide tagged with the first member of a first specific binding pair is annealed and ligated to the single-stranded ends generated in the digestion reaction. The reaction is contacted with the second member of the first specific binding pair, immobilized on a first solid support. The material not bound to the first solid support is denatured, and contacted with a second oligonucleotide complementary to a sequence in the strand of the PCR product containing the detectable label. The sequence is between the polymorphic restriction site and either the sequence corresponding to the first primer or the sequence complementary to the second primer, and the second oligonucleotide is immobilized on a second solid support (e.g., a nylon or nitrocellulose membrane).

The ratio of the level of the detectable label bound to the first solid support to the level of the detectable label bound to the second solid support is then determined. A ratio of 1:0 is an indication of a homozygote containing the polymorphic restriction site, a ratio of 0:1 is an indication of a homozygote lacking the polymorphic restriction site, and a ratio of 1:1 is an indication of a heterozygote. These ratios are correct in cases where the total amount of the material not bound to the first solid support is used in the following steps, and should be adjusted accordingly, if a different amount of the material is used. An embodiment of this method is shown in FIG. 6.

PCR primers containing nucleic acid tags on their 5' ends can also be used in the methods of the invention. These primers can be used in pairs, or in combination with un-tagged primers, in the initial cycles of PCR, followed by the addition of a "universal primer(s)" complementary to the nucleic acid tags in the first primers, and contain detectable labels (e.g., biotin, fluorescent, or ELISA tags). The use of nucleic acid tagged primers in the early rounds of PCR is a cost-effective measure, as only one set of primers, the universal primers, which can be used in the analysis of many different polymorphic sites, need to be detectably labeled. The sets of primers specific for individual polymorphic restriction sites do not have to be tagged with detectable labels, but rather need only to be complementary to the universal primers in their 5' ends.

Example IX

Figure 7:
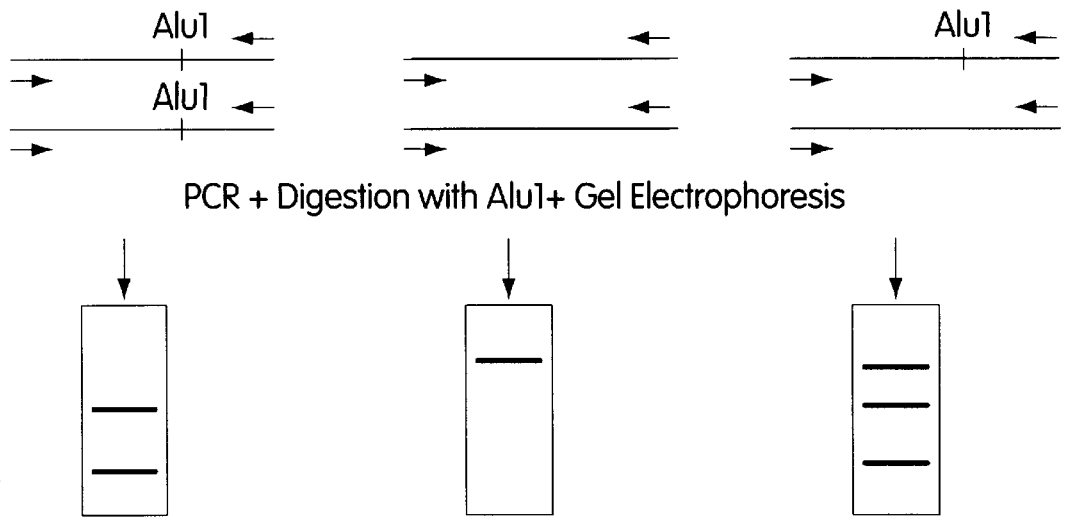

In another method of the invention, the nucleic acid is amplified by PCR using a first and a second primer flanking the polymorphic restriction site. The PCR product is digested with the restriction endonuclease corresponding to the polymorphic restriction site, and, as shown in FIG. 7, the digestion products are run on a gel (preferably an agarose gel). To simplify the gel reading, the first and second primers are preferably designed to generate a PCR product that is easily resolvable on an agarose gel (e.g., preferably larger than 100 base pairs and smaller than 1000 base pairs), and the polymorphic restriction site is preferably located at an asymmetric position within the amplified fragment. Using this technique, short gel runs can be used for analysis, and the cleaved products are easily detected. In the particular example shown in FIG. 8, primers are designed to produce PCR amplified products of 300 base pairs, and cleavage at the RFLP site yields products of 200 base pairs and 100 base pairs.

Figure 8:
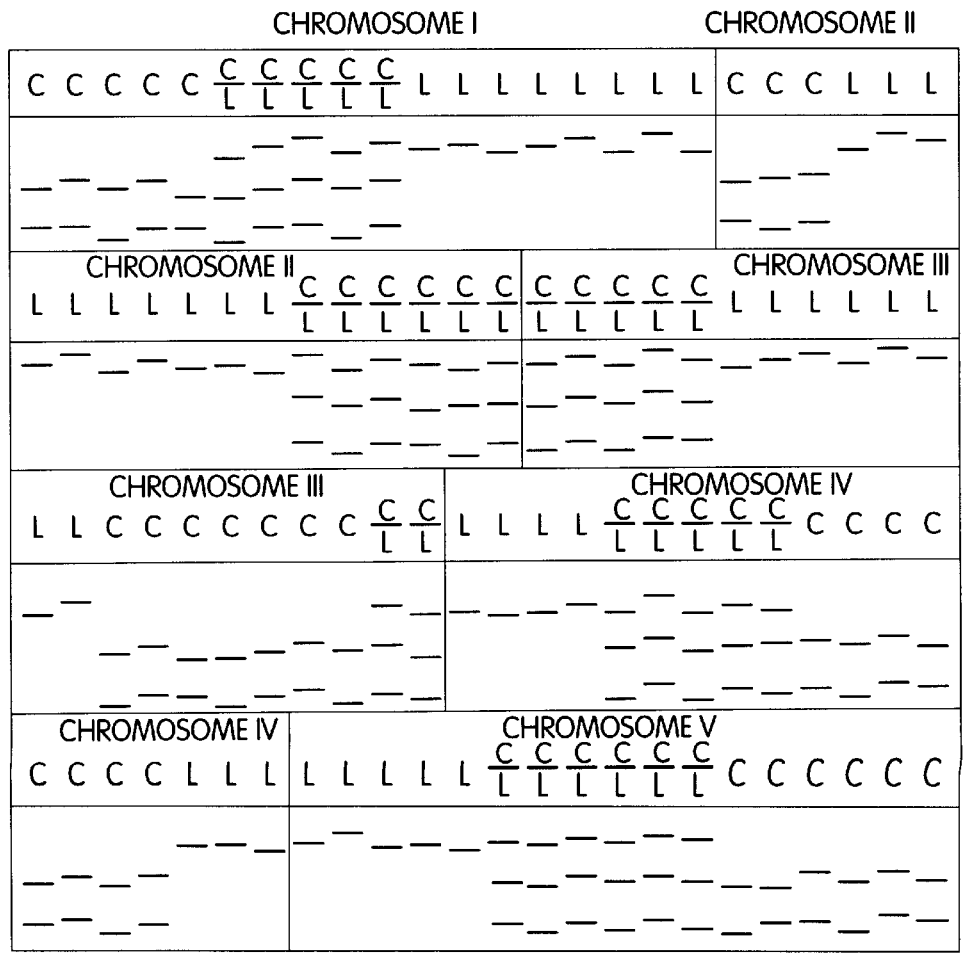
FIG. 8 is a schematic of a typical gel analysis according to the method described in FIG. 7.
Figure 9E:
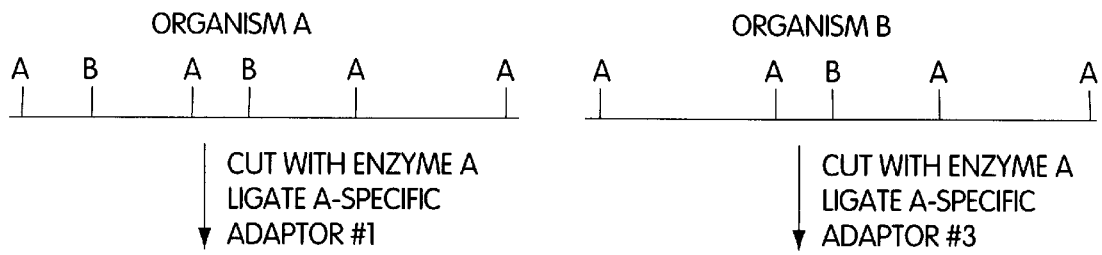
Figure 9E:
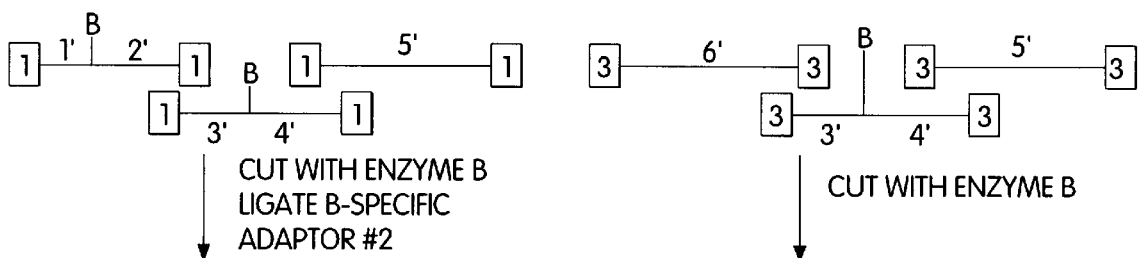
Figure 9E:
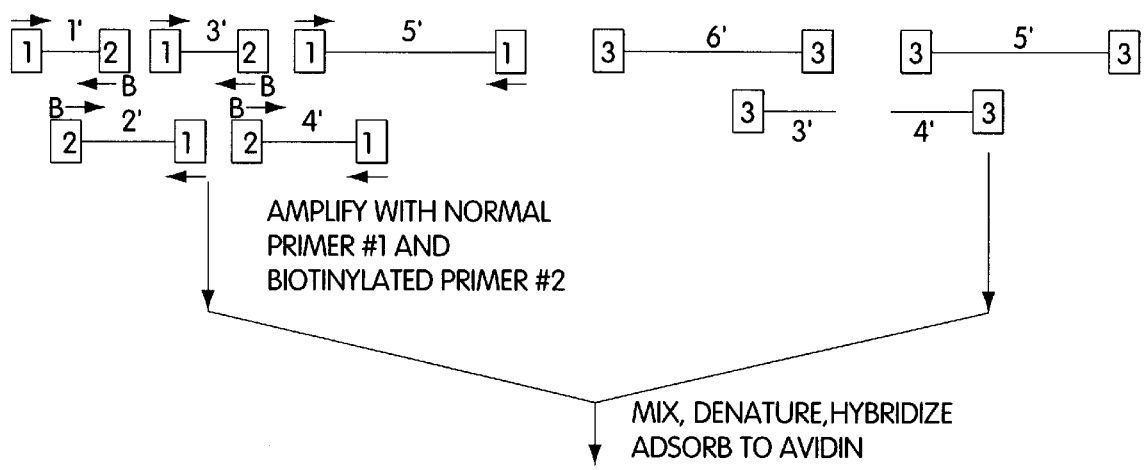
Figure 9E:
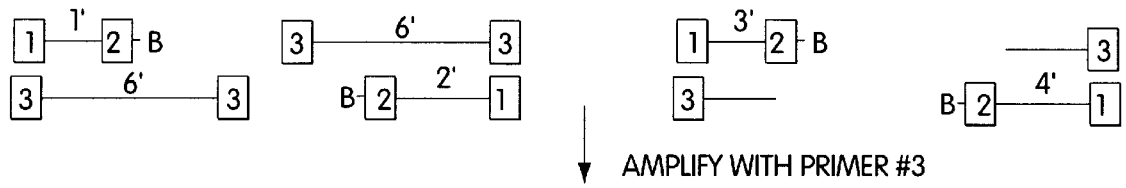
Figure 9E:
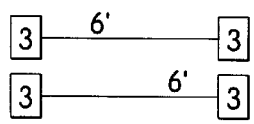

In a preferred method of carrying out this method, sets of primer pairs are provided that detect a number of RFLP markers. Each set of primers may be provided, for example, in one of the wells of a 96-well microtiter plate, and PCR reactions run independently. Following restriction digestion, the reaction products are transferred to an agarose gel and separated by electrophoresis. A typical result of this method is shown in FIG. 8.

Detection of the amplified and cleaved products after electrophoretic separation can be carried out by standard methods of DNA staining (e.g., ethidium bromide staining) or blotting (e.g., Southern blotting). Alternatively, one or both of the PCR primers can be detectably labeled, and the labels can be detected as described above.

Example X

A preferred use of the methods of the invention is in conjunction with a method called RFLP subtraction. RFLP subtraction provides a large number of polymorphic genetic markers, while the methods of the present invention provide efficient methods for their analysis.

Carrying out RFLP subtraction results in the purification of fragments that are present in one population (the tracer) but absent in another (the driver). Purification is achieved by removing all of the fragments in the tracer DNA that have counterparts in the driver DNA using subtractive hybridization (Innis et al., PCR Protocols: A Guide to Methods and Applications, Academic Press, Harcourt Brace Javanovich, New York, 1990). In RFLP subtraction, the tracer is a size fraction of digested DNA from one strain and the driver is the same size fraction from a polymorphic strain. The products obtained after removing the common sequences are RFLPs; they are sized tracer fragments whose driver counterparts are not found in the same size fraction.

There are three steps in RFLP subtraction: preparation of the driver and tracer, subtractive hybridization, and removal of non-hybridizing sequences from the tracer. To prepare the driver and tracer DNA, genomic DNA from two different strains is digested with a restriction endonuclease, and the ends of the restriction fragments from each strain are capped with different oligonucleotide adapters. The low molecular weight fragments are then purified from a slice of an agarose gel and amplified using one of the adapter strands as a PCR primer. A biotinylated primer can be used to amplify the driver so that driver DNA can be removed following the subtractive hybridizations by binding to avidin coated beads.

Three rounds of subtractive hybridization are performed to remove tracer sequences that also occur in the driver. A small amount of tracer is mixed with an excess of biotinylated driver, the mixture is denatured and allowed to re-anneal. Most tracer sequences will hybridize to complementary biotinylated driver strands. Some tracer sequences, however, are not represented in the driver because they reside on large restriction fragments (i.e., they are RFLPs) or are missing from the driver genome. These fragments will have no complementary biotinylated strands with which to anneal The biotinylated driver DNA, and any tracer that has annealed to it, is then removed using avidin-coated beads. The unbound fraction is then subjected to two more rounds of subtractive hybridization, tracer DNA remaining after the third round is amplified, and poorly hybridizing sequences are removed.

Example XI

FIG. 9 shows a preferred method for cloning polymorphic restriction fragments. The object of this method is to clone restriction fragments from organism B (generated by restriction endonuclease A) that do not contain cleavage sites for restriction endonuclease B, and which correspond to restriction fragments in organism A (generated by restriction endonuclease A) that do contain at least one restriction site for restriction endonuclease B. These polymorphic restriction fragments are useful as CAPS markers for the detection methods described above.

Referring to the method outlined in FIG. 9, in step A, genomic DNA isolated from polymorphic individuals A and B is separately digested with restriction enzyme A, which preferably leaves so-called sticky ends. An oligonucleotide adaptor (#1), with complementary sticky ends, is ligated to the restriction fragments from individual A. A different oligonucleotide adaptor (#3) is ligated to the restriction fragments from individual B.

In step B, the restriction fragments from step A are cleaved with restriction endonuclease B, which again preferably leaves sticky ends. In the case of the DNA fragments from individual A, an oligonucleotide adaptor (#2), with complementary sticky ends for enzyme B, is ligated to the restriction fragments generated by cleavage with enzyme B.

In step C, the DNA fragments from individual A are amplified using the PCR with an oligonucleotide primer complementary to adaptor #1 and with a biotinylated oligonucleotide primer complementary to adaptor #2.

In step D, the amplified products originating from individual A are mixed with the non-amplified fragments of step B from individual B. The mixed DNA fragments are then heat denatured, annealed, and adsorbed onto an avidin-coated solid support (e.g., beads). The avidin coated support containing the adsorbed fragments is thoroughly washed. If desired, the adsorbed fragments may be eluted, re-amplified with the same primers as above, adsorbed onto a fresh avidin-containing support, and thoroughly washed. This step can be repeated as many times as is necessary or desired.

In step E, the fragments adsorbed to the avidin-coated beads are eluted and amplified using PCR with primers complementary to adaptor #3. The amplified products should correspond to the desired restriction fragments described above. These amplified fragments are cloned and then tested individually using the Southern DNA blot hybridization method for their ability to display the desired RFLP.

Example XII

In this method, the nucleic acid is amplified by PCR using a first and a second primer flanking the polymorphic restriction site, with the first primer being tagged with a detectable label. The amplification generates a PCR product containing a first strand tagged with the detectable label and a second, unlabeled strand. The PCR product is digested with the restriction endonuclease corresponding to the polymorphic restriction site and the digestion product is denatured. The denatured product is contacted with a first probe that (1) contains a sequence that hybridizes to a first sequence in the first strand of the PCR product, and (2) is immobilized on a first binding element. The first sequence is between the polymorphic restriction site and the sequence in the first strand that is complementary to the second primer.

The first binding element is monitored for the presence of the detectable label. Detection of the detectable label on the first binding element indicates the absence of the polymorphic restriction site in the nucleic acid, and a failure to detect the detectable label on the first binding element indicates the presence of the polymorphic restriction site in the nucleic acid.

In addition to the first probe described above, this method can employ the use of a second, a third, or a fourth probe. The second probe contains a sequence that hybridizes to a second sequence which is in the first strand and is between the polymorphic restriction site and the sequence in the first strand that corresponds to the first primer. The third probe contains a sequence that hybridizes to a third sequence which is in the second strand and is between the polymorphic restriction site and the sequence in the second strand corresponding to the second primer. The fourth probe contains a sequence that hybridizes to a fourth sequence which is in the second strand and is between the polymorphic restriction site and the sequence in the second strand that is complementary to the first primer. The second, third, and fourth probes are immobilized on a second, third, and fourth binding element, respectively. The second binding element can be monitored for the presence of the detectable label as a positive control, while the third or fourth binding elements can be monitored for the presence of the detectable label as negative controls. The first, second, third, and fourth binding elements, in this and in other methods of the invention, can be present on a solid support having similar sets of binding elements for testing different nucleic acids (see, for example, FIG. 11).

The binding elements, for example, the first, second, third, and fourth binding elements, used in this method of the invention can be present as distinct regions on a single solid support. For example, they can be specific sets of nucleic acids bound to distinct regions on a glass plate or on a microchip, such as a glass, silicon, or glass-silicon microchip (see above).

Example XIII

In this method a nucleic acid is amplified by PCR using a first and a second primer flanking the polymorphic restriction site. The first primer is tagged with a first detectable label and the second primer is tagged with a second detectable label. The amplification thus generates a PCR product containing a first strand tagged with the first detectable label and a second strand tagged with the second detectable label. In this method, the first and second labels can be identical or distinct.

The PCR product is treated with a restriction endonuclease corresponding to the polymorphic restriction site to generate a digestion product, which is denatured to generate a denatured product. The denatured product is contacted with a first and a second probe. The first probe, which is immobilized on a first binding element, contains a sequence that hybridizes to a first sequence in the first strand that is between the polymorphic restriction site and the sequence in the first strand that is complementary to the second primer. The second probe, which is immobilized on a second binding element, contains a sequence that hybridizes to a second sequence in the second strand that is between the polymorphic restriction site and the sequence in the second strand that is complementary to the first primer.

The first binding element is monitored for the presence of the first detectable label and the second binding element is monitored for the presence of the second detectable label. Detection of the first detectable label on the first binding element and detection of the second detectable label on the second binding element indicates the absence of the polymorphic restriction site in the nucleic acid, while a failure to detect the first detectable label on the first binding element and a failure to detect the second detectable label on the second binding element indicates the presence of the polymorphic restriction site in the nucleic acid.

In addition to the first and second probes described above, this method can involve the use of a third and fourth probe. The third probe, which is immobilized on a third binding element, contains a sequence that hybridizes to a third sequence which is in the first strand and that is between the polymorphic restriction site and the sequence in the first strand corresponding to the first primer. The fourth probe, which is immobilized on a fourth binding element, contains a sequence that hybridizes to a fourth sequence which is in the second strand and that is between the polymorphic restriction site and the sequence in the second strand corresponding to the second primer.

The third or fourth binding elements can be monitored for the presence of the first or second detectable labels as controls. For example, the third binding element can be monitored for the presence of the first detectable label and the fourth binding element can be monitored for the presence of the second detectable label.

Figure 10:
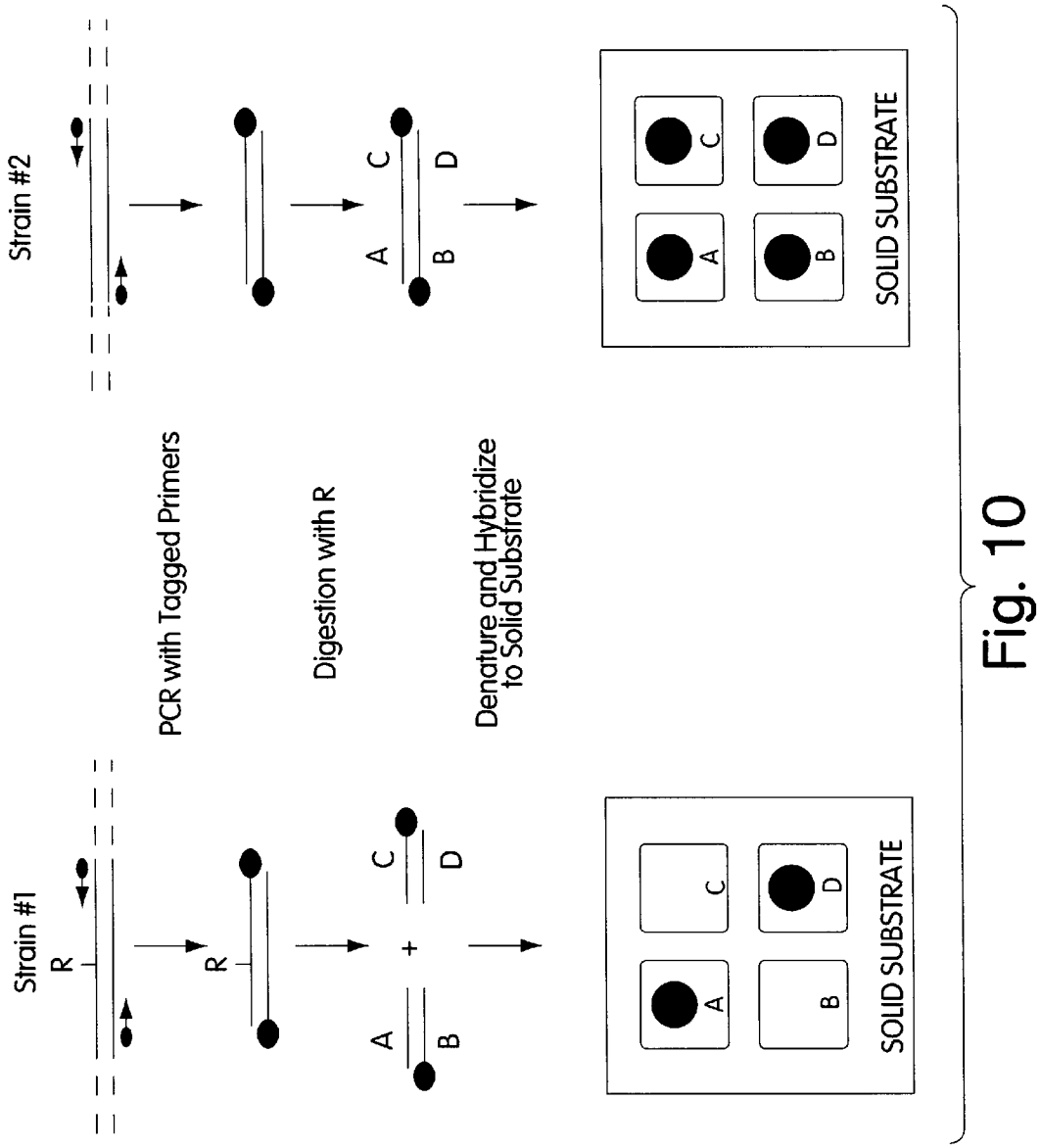
FIG. 10 is a schematic of a non-gel based method for detection of CAPS markers.
Figure 11:
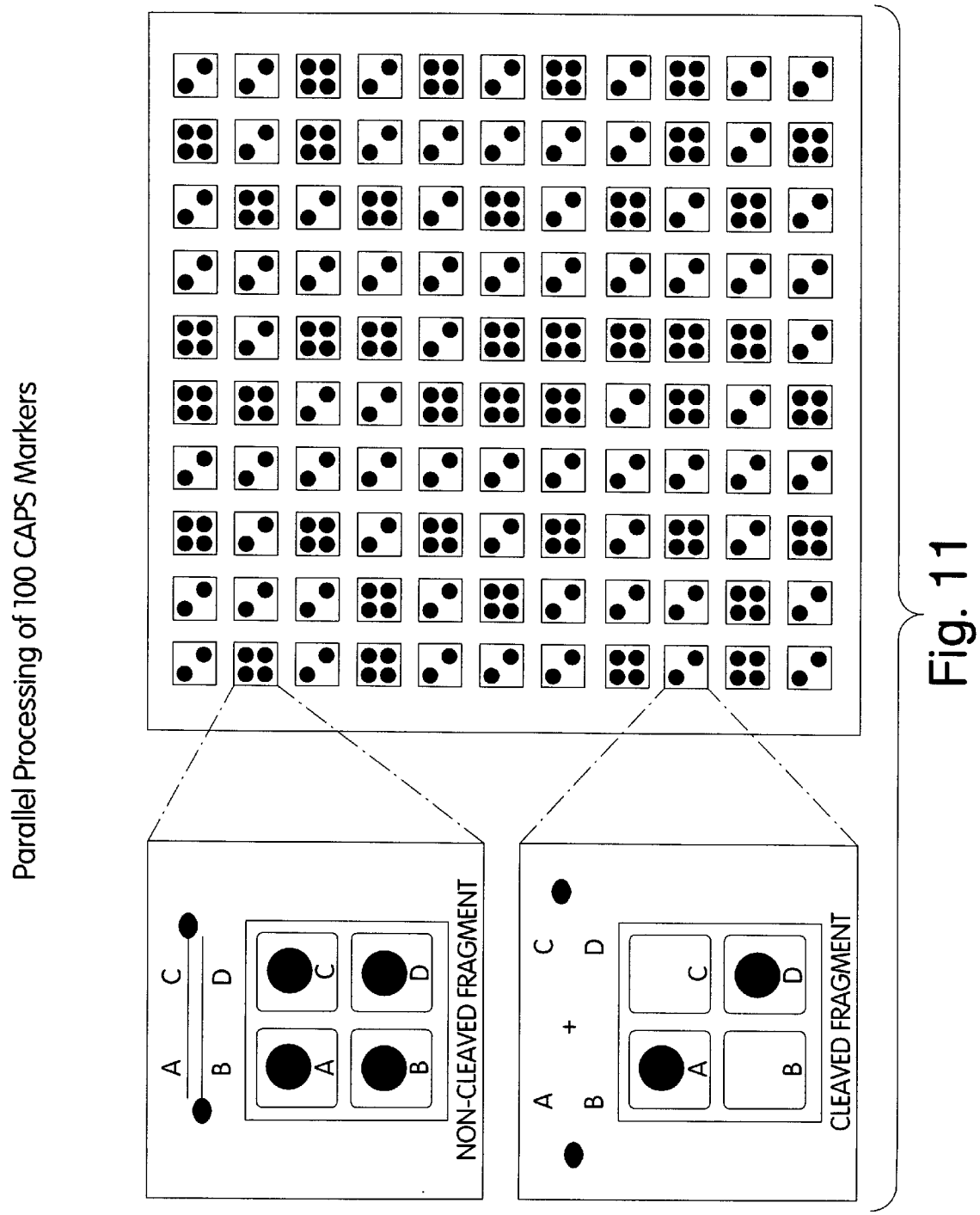
FIG. 11 is a schematic of parallel processing of 100 CAPS markers on a microchip containing an array of oligonucleotide probes.

The first and seconds or the first, second, third, and fourth binding elements can be present as distinct regions on a solid support, such as glass (e.g., a glass plate) or a microchip (e.g., a silicon or a silicon-glass microchip). Embodiments of this method are illustrated in FIGS. 10 and 11.

Example XIV

In this method, the nucleic acid is amplified by PCR using a first and a second primer flanking the polymorphic restriction site. The amplification generates a PCR product containing a first strand containing a sequence corresponding to the first primer and a second strand containing a sequence corresponding to the second primer.

The PCR product is treated with a restriction endonuclease corresponding to the polymorphic restriction site to generate a digestion product, which is denatured to generate a denatured product. The denatured product is contacted with an oligonucleotide to generate a first reaction product. The oligonucleotide contains a 3' portion that hybridizes to a first region in the first strand that flanks the polymorphic restriction site on the side of the polymorphic restriction site containing a sequence corresponding to the first primer. The 3' end of the oligonucleotide is blocked by, e.g., a di-deoxynucleotide, so that it cannot serve as a primer for DNA polymerase. The oligonucleotide contains a 5' portion that does not hybridize to a second region in the first strand that flanks the polymorphic restriction site on the side of the polymorphic restriction site containing a sequence that is complementary to the second primer. The use of such an oligonucleotide to label a cleaved end of a CAPS marker is illustrated in FIG. 12.

As illustrated in FIG. 12., the first reaction product is treated with a DNA polymerase to extend the unblocked, primed 3' end to generate a second reaction product, which is amplified by PCR using the first primer, tagged with a first detectable label, and a third primer, which hybridizes to a sequence that is complementary to the 5' portion of the oligonucleotide, to generate a second PCR product. The third primer is tagged with a second detectable label. In this method, the first and second detectable labels can be identical or distinct.

The second PCR product is denatured to generate a second denatured product, which is contacted with a first and a second probe. The first probe, which is immobilized on a first binding element, contains a sequence that hybridizes to a first sequence in the second strand that is between the polymorphic restriction site and the sequence in the second strand that is complementary to the first primer. The second probe, which is immobilized on a second binding element, contains a sequence that hybridizes to a second sequence in the first strand that is between the polymorphic restriction site and the sequence in the first strand that is complementary to the second primer.

The first binding element is monitored for the presence of the second detectable label and the second binding element is monitored for the presence of the first detectable label. Detection of the second detectable label on the first binding element and detection of the first detectable label on the second binding element indicates a heterozygote, detection of the second detectable label on the first binding element and a failure to detect the first detectable label on the second binding element indicates a homozygote containing the polymorphic restriction site, and detection of the first detectable label on the second binding element and a failure to detect the second detectable label on the first binding element indicates a homozygote lacking the polymorphic restriction site.

In addition to the first and second probes described above, this method can employ a third or a fourth probe. The third probe, which is immobilized on a third binding element, contains a sequence that hybridizes to a third sequence in the first strand that is between the polymorphic restriction site and the sequence in the first strand corresponding to the first primer. The fourth probe, which is immobilized on a fourth binding element, contains a sequence that hybridizes to a fourth sequence in the second strand that is between the polymorphic restriction site and the sequence in the second strand corresponding to the second primer.

The third or fourth binding elements can be monitored for the presence of the first or second detectable labels as controls. For example, the third binding element can be monitored for the presence of the first detectable label.

The first and second, or the first, second, third, and fourth binding elements can be present as distinct regions on a solid support, such as a glass (e.g., a glass plate) or silicon (e.g., a microchip) support.

Figure 13:
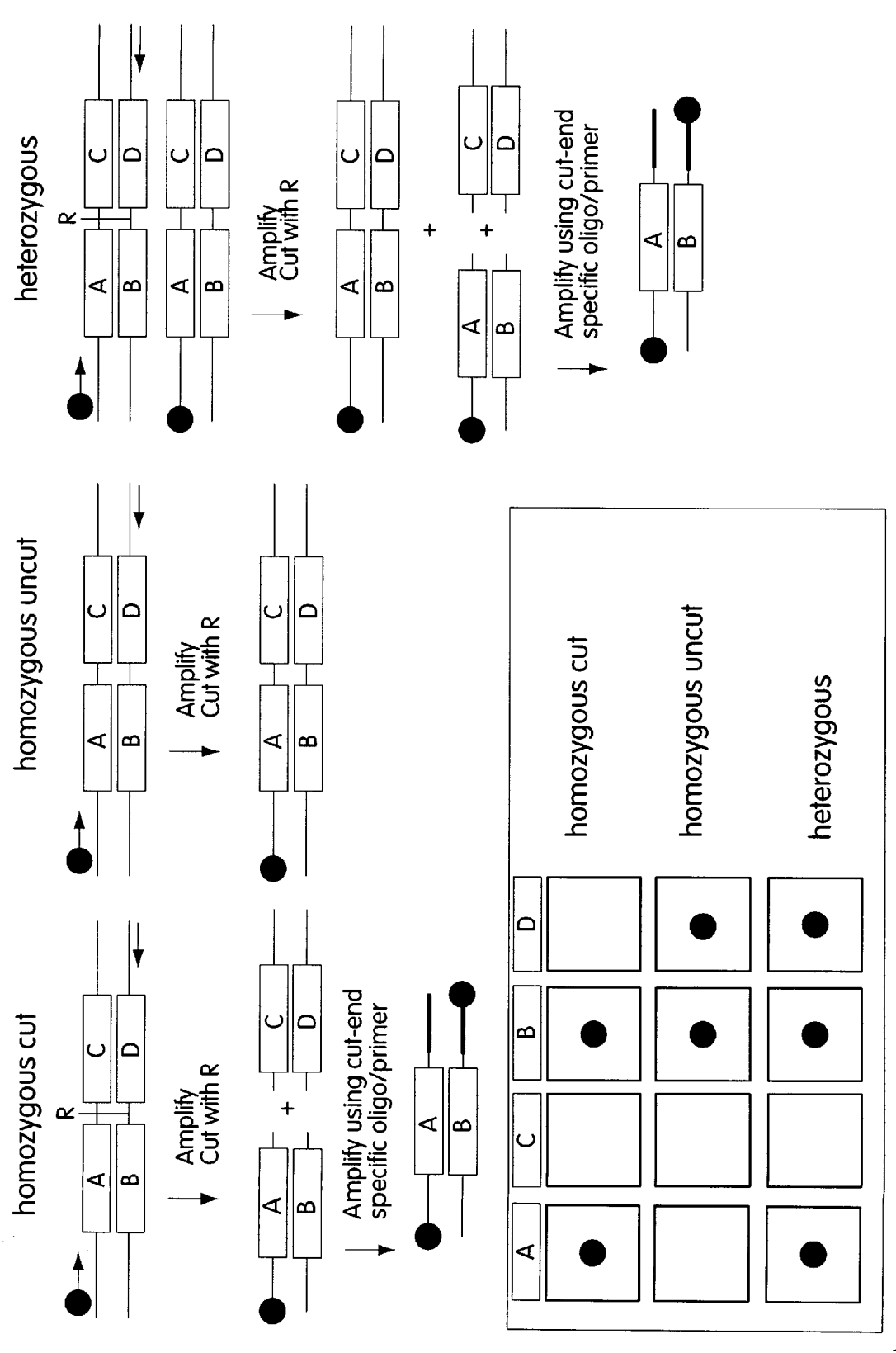
FIG. 13 is a schematic of a method for distinguishing heterozygous CAPS alleles from homozygous CAPS alleles, involving the use of the method for detecting a cleaved end of a CAPS marker shown in FIG. 12.

This embodiment is illustrated in FIG. 13.

Use of oligonucleotides as described above provides several advantages. For example, because there can be a significant amount of overlap between the oligonucleotide and the cleaved product, highly stringent conditions can be used in the annealing reaction, leading to increased specificity. In addition, the 5' end of the oligonucleotide can be the same for many CAPS markers, as it is by design not homologous to any amplified sequences corresponding to a CAPS marker for an organism of interest. These advantages also apply to other methods employing such an oligonucleotide, as are described below.

OTHER EMBODIMENTS

The above examples are, therefore, to be construed as merely illustrative, and not limitative of the remainder of the disclosure in any way whatsoever.

From the above description, one skilled in the art can easily ascertain the essential characteristics of the present invention, and without departing form the spirit and scope thereof, can make various changes and modifications of the invention to adapt it to various usages and conditions. All publications cited herein are fully incorporated by reference herein in their entirety. Other embodiments are in the claims set forth below.

What is claimed is:

1. A method for identifying a polymorphic restriction site in a nucleic acid, said method comprising the steps of:
   (a) digesting DNA isolated from a first sample of an organism with a first restriction endonuclease to generate a first reaction product;
   (b) ligating to each of the ends of said first reaction product a first adaptor to generate a second reaction product;
   (c) digesting said second reaction product with a second restriction endonuclease to generate a third reaction product;
   (d) ligating to each of the ends of said third reaction product a second adaptor to generate a fourth reaction product;
   (e) amplifying said fourth reaction product to generate a fifth reaction product by PCR using a first primer complementary to said first adaptor and a second primer complementary to said second adaptor, said second primer being tagged with a first member of a specific binding pair;
   (f) in a separate set of reactions, digesting DNA isolated from a second sample from said organism with said first restriction endonuclease to generate a sixth reaction product;
   (g) ligating to each of the ends of said sixth reaction product a third adaptor to generate a seventh reaction product;
   (h) digesting said seventh reaction product with said second restriction endonuclease to generate an eighth reaction product;

(i) denaturing said fifth reaction product to generate a ninth reaction product and denaturing said eighth reaction product to generate a tenth reaction product;

(j) combining said ninth and tenth reaction products under conditions allowing hybridization to generate an eleventh reaction product;

(k) contacting said eleventh reaction product with the second member of said specific binding pair, said second member being immobilized on a solid support;

(l) recovering any of said eleventh reaction product captured on said solid support to generate a twelfth reaction product; and (m) amplifying said twelfth reaction product by PCR using a primer complementary to said third adaptor, an amplified product being an indication of a polymorphic restriction site that is recognized by said second restriction endonuclease.

2. The method of claim 1, wherein said specific binding pair is avidin and biotin.

3. A kit for identifying a polymoiphic restriction site in a nucleic acid, said kit comprising:

(a) a first DNA adaptor, a second DNA adaptor, and a third DNA adaptor, said first and third DNA adaptors comprising regions complementary to the ends generated by a first restriction endonuclease ends but differing in overall sequence and said second DNA adaptor comprising a region complementary to the ends generated by a second restriction endonuclease, said second restriction endonuclease site corresponding to said polymorphic restriction site; and (b) a first primer, a second primer, and a third primer, said first primer hybridizing to said first DNA adaptor, said second primer hybridizing to said second DNA adaptor and being tagged with a first member of a specific binding pair, and said third primer hybridizing to said third DNA adaptor.

4. The kit of claim 3, wherein said kit further comprises the second member of said specific binding pair immobilized on a solid support.

5. A method for detecting the presence or absence of a polymorphic restriction site in a nucleic acid, said method comprising the steps of:

(a) amplifying said nucleic acid by PCR using a first and a second primer flanking said polymorphic restriction site, said first primer being tagged with a detectable label, wherein said amplifying generates a PCR product comprising a first strand tagged with said detectable label and an unlabeled second strand;

(b) treating said PCR product with a restriction endonuclease that recognizes said polymorphic restriction site to generate a digestion product;

(c) denaturing said digestion product to generate a denatured product;

(d) contacting said denatured product with a first probe, said first probe comprising a sequence that hybridizes to a first sequence in said first strand, said first sequence being between said polymorphic restriction site and the sequence in said first strand that is complementary to said second primer, said first probe being immobilized on a first binding element;

(e) monitoring said first binding element for the presence of said detectable label, wherein detection of said detectable label on said first binding element indicates the absence of said polymorphic restriction site in said nucleic acid, and a failure to detect said detectable label on said first binding element indicates the presence of said polymorphic restriction site in said nucleic acid.

6. The method of claim 5, further comprising the steps of:

(a) contacting said denatured product with a second, a third, or a fourth probe, said second probe comprising a sequence that hybridizes to a second sequence in said first strand, said second sequence being between said polymorphic restriction site and the sequence in said first strand that is identical to said first primer, said second probe being immobilized on a second binding element; said third probe comprising a sequence that hybridizes to a third sequence in said second strand, said third sequence being between said polymorphic restriction site and the sequence in said second strand that is identical to the sequence of said second primer, said third probe being immobilized on a third binding element; said fourth probe comprising a sequence that hybridizes to a fourth sequence in said second strand, said fourth sequence being between said polymorphic restriction site and the sequence in said second strand that is complementary to said first primer, said fourth probe being immobilized on a fourth binding element; and (b) monitoring said second, third, or fourth binding element for the presence of said detectable label.

7. The method of claim 5, wherein said first binding element is a region on a solid support.

8. The method of claim 7, wherein said solid support is glass.

9. The method of claim 7, wherein said solid support is a microchip.

10. The method of claim 6, wherein said first, second, third, and fourth binding elements are each distinct regions on a solid support.

11. The method of claim 10, wherein said solid support is glass.

12. The method of claim 10, wherein said solid support is a microchip.

13. A method for detecting the presence or absence of a polymorphic restriction site in a nucleic acid, said method comprising the steps of:

(a) amplifying said nucleic acid by PCR using a first and a second primer flanking said polymorphic restriction site, said first primer being tagged with a first detectable label, said second primer being tagged with a second detectable label, wherein said amplifying generates a PCR product comprising a first strand tagged with said first detectable label and a second strand tagged with said second detectable label;

(b) treating said PCR product with a restriction endonuclease that recognizes said polymorphic restriction site to generate a digestion product;

(c) denaturing said digestion product to generate a denatured product;

(d) contacting said denatured product with a first and a second probe, said first probe comprising a sequence that hybridizes to a first sequence in said first strand, said first sequence being between said polymorphic restriction site and the sequence in said first strand that is complementary to said second primer, said first probe being immobilized on a first binding element; said second probe comprising a sequence that hybridizes to a second sequence in said second strand, said second sequence being between said polymorphic restriction site and the sequence in said second strand that is complementary to said first primer, said second probe being immobilized on a second binding element;

(e) monitoring said first binding element for the presence of said first detectable label and monitoring said second binding element for the presence of said second detectable label, wherein detection of said first detectable label on said first binding element and detection of said second detectable label on said second binding element indicates the absence of said polymorphic restriction site in said nucleic acid, and a failure to detect said first detectable label on said first binding element and a failure to detect said second detectable label on said second binding element indicates the presence of said polymorphic restriction site in said nucleic acid.

14. The method of claim 13, further comprising the steps of:

(a) contacting said denatured product with a third or a fourth probe, said third probe comprising a sequence that hybridizes to a third sequence in said first strand, said third sequence being between said polymorphic restriction site and the sequence in said first strand that is identical to the sequence of said first primer, said third probe being immobilized on a third binding element; said fourth probe comprising a sequence that hybridizes to a fourth sequence in said second strand, said fourth sequence being between said polymorphic restriction site and the sequence in said second strand that is identical to the sequence of said second primer, said fourth probe being immobilized on a fourth binding element; and (b) monitoring said third or fourth binding element for the presence of said first or second detectable label.

15. The method of claim 13, wherein said first and said second detectable labels are identical.

16. The method of claim 13, wherein said first and second binding elements are each distinct regions on a solid support.

17. The method of claim 16, wherein said solid support is glass.

18. The method of claim 16, wherein said solid support is a microchip.

19. The method of claim 14, wherein said first, second, third, and fourth binding elements are each distinct regions on a solid support.

20. The method of claim 19, wherein said solid support is glass.

21. The method of claim 19, wherein said solid support is a microchip.

22. A method for determining whether an organism is homozygous for a polymorphic restriction site, is heterozygous for said polymorphic restriction site, or lacks said polymorphic restriction site, said method comprising the steps of:

(a) carrying out PCR on a sample comprising nucleic acid molecules from the organism using a first and a second primer flanking said polymorphic restriction site, wherein said amplifying generates a PCR product comprising a first strand comprising a sequence that is identical to the sequence of said first primer and a second strand comprising a sequence that is identical to the sequence of said second primer;

(b) treating said PCR product with a restriction endonuclease that recognizes said polymorphic restriction site to generate a digestion product;

(c) denaturing said digestion product to generate a denatured product;

(d) contacting said denatured product with an oligonucleotide to generate a first reaction product, said oligonucleotide comprising a 3' portion that hybridizes to a first region in said first strand, said first region being between said polymorphic restriction site and a sequence in said first strand that is identical to the sequence of said first primer, said oligonucleotide being blocked so that it cannot serve as a primer for DNA polymerase, said oligonucleotide comprising a 5' portion that does not hybridize to said first strand;

(e) treating said first reaction product with a DNA polymerase to extend any unblocked, primed 3' end in said first reaction product to generate a second reaction product;

(f) amplifying said second reaction product by PCR using a third primer, said third primer having a sequence identical to said first primer and being tagged with a first detectable label, and a fourth primer that hybridizes to a sequence that is complementary to said 5' portion of said oligonucleotide to generate a second PCR product, said fourth primer being tagged with a second detectable label;

(g) denaturing said second PCR product to generate a second denatured product;

(h) contacting said second denatured product with a first and a second probe, said first probe comprising a sequence that hybridizes to a first sequence in said second strand, said first sequence being between said polymorphic restriction site and the sequence in said second strand that is complementary to said first primer, said first probe being immobilized on a first binding element; said second probe comprising a sequence that hybridizes to a second sequence in said first strand, said second sequence being between said polymorphic restriction site and the sequence in said first strand that is complementary to said second primer, said second probe being immobilized on a second binding element;

(i) monitoring said first binding element for the presence of said second detectable label and monitoring said second binding element for the presence of said first detectable label, wherein detection of said second detectable label on said first binding element and detection of said first detectable label on said second binding element indicates that the organism is heterozygous for said polymorphic restriction site, detection of said second detectable label on said first binding element and a failure to detect said first detectable label on said second binding element indicates that the organism is a homozygote comprising said polymorphic restriction site, and detection of said first detectable label on said second binding element and a failure to detect said second detectable label on said first binding element indicates that the organism is a homozygote lacking said polymorphic restriction site.

23. The method of claim 22, further comprising the steps of:

(a) contacting said second denatured product with a third or a fourth probe, said third probe comprising a sequence that hybridizes to a third sequence in said first strand, said third sequence being between said polymorphic restriction site and the sequence in said first strand that is identical to the sequence of said first primer, said third probe being immobilized on a third binding element; said fourth probe comprising a sequence that hybridizes to a fourth sequence in said second strand, said fourth sequence being between said polymorphic restriction site and the sequence in said second strand that is identical to the sequence of said second primer, said fourth probe being immobilized on a fourth binding element; and (b) monitoring said third or fourth binding element for the presence of said first or second detectable label.

24. The method of claim 22, wherein said first and said second detectable labels are identical.

25. The method of claim 22, wherein said first and second binding elements are each distinct regions on a solid support.

26. The method of claim 25, wherein said solid support is glass.

27. The method of claim 25, wherein said solid support is a microchip.

28. The method of claim 23, wherein said first, second, third, and fourth binding elements are each distinct regions on a solid support.

29. The method of claim 28, wherein said solid support is glass.

30. The method of claim 28, wherein said solid support is a microchip.

31. A kit for detecting the presence or absence of a polymorphic restriction site in a nucleic acid, said kit comprising:

a first and a second primer flanking said polymorphic restriction site, said first primer being tagged with a detectable label, wherein amplifying said nucleic acid by PCR with said first and second primers generates a PCR product comprising a first strand tagged with said detectable label and a second strand; and a first probe that comprises a sequence that hybridizes to a first sequence in said first strand, said first sequence being between said polymorphic restriction site and the sequence in said first strand that is complementary to said second primer, and said first probe is immobilized on a first binding element.

32. The kit of claim 31, further comprising a second, third, or fourth probe, said second probe comprising a sequence that hybridizes to a second sequence in said first strand, said second sequence being between said polymorphic restriction site and the sequence in said first strand that is identical to the sequence of said first primer, said second probe being immobilized on a second binding element; said third probe comprising a sequence that hybridizes to a third sequence in said second strand, said third sequence being between said polymorphic restriction site and the sequence in said second strand that is identical to the sequence of said second primer, said third probe being immobilized on a third binding element; and said fourth probe comprising a sequence that hybridizes to a fourth sequence in said second strand, said fourth sequence being between said polymorphic restriction site and the sequence in said second strand that is complementary to said first primer, said fourth probe being immobilized on a fourth binding element.

33. The kit of claim 31, wherein said first binding element is a region on a solid support.

34. The kit of claim 32, wherein said solid support is glass.

35. The kit of claim 32, wherein said solid support is a microchip.

36. The kit of claim 31, wherein said first, second, third, and fourth binding elements are each distinct regions on a solid support.

37. The kit of claim 36, wherein said solid support is glass.

38. The kit of claim 36, wherein said solid support is a microchip.

39. The kit of claim 31, wherein said second primer comprises a second detectable label and said kit further comprises a second probe comprising a sequence that hybridizes to a second sequence in said second strand, said second sequence being between said polymorphic restriction site and the sequence in said second strand that is complementary to said first primer, and said second probe being immobilized on a second binding element.

40. The kit of claim 39, further comprising a third or a fourth probe, said third probe comprising a sequence that hybridizes to a third sequence in said first strand, said third sequence being between said polymorphic restriction site and the sequence in said first strand that is identical to the sequence of said first primer, said third probe being immobilized on a third binding element; said fourth probe comprising a sequence that hybridizes to a fourth sequence in said second strand, said fourth sequence being between said polymorphic restriction site and the sequence in said second strand that is identical to the sequence of said second primer, and said fourth probe being immobilized on a fourth binding element.

41. The kit of claim 31, further comprising a second probe comprising a sequence that hybridizes to a second sequence in said first strand, said second sequence being between said polymorphic restriction site and the sequence in said first strand that is identical to said first primer, and said second probe being immobilized on a second binding element.

42. A kit for detecting the presence or absence of a polymorphic restriction site in a nucleic acid, said kit comprising:

a first and a second PCR primer flanking said polymorphic restriction site, said first primer being tagged with a first detectable label, wherein amplifying said nucleic acid by PCR using said first and second primers generates a PCR product comprising a first strand tagged with said first detectable label and a second strand;

an oligonucleotide comprising a 3' portion that hybridizes to a first region in said first strand, said first region flanking said polymorphic restriction site on the side of said polymorphic restriction site comprising a sequence that is identical to the sequence of said first primer, said oligonucleotide being blocked so that it cannot serve as a primer for DNA polymerase, said oligonucleotide comprising a 5' portion that does not hybridize to a second region in said first strand, said second region flanking said polymorphic restriction site on the side of said polymorphic restriction site comprising a sequence that is complementary to said second primer;

a third primer that hybridizes to a sequence that is complementary to said 5' portion of said oligonucleotide, said third primer being tagged with a second detectable label;

a first and a second probe, said first probe comprising a sequence that hybridizes to a first sequence in said second strand, said first sequence being between said polymorphic restriction site and the sequence in said second strand that is complementary to said first primer, said first probe being immobilized on a first binding element; said second probe comprising a sequence that hybridizes to a second sequence in said first strand, said second sequence being between said polymorphic restriction site and the sequence in said first strand that is complementary to said second primer, and said second probe being immobilized on a second binding element.

43. The kit of claim 42, further comprising a third or a fourth probe, said third probe comprising a sequence that hybridizes to a third sequence in said first strand, said third sequence being between said polymorphic restriction site and the sequence in said first strand that is identical to the sequence of said first primer, said third probe being immobilized on a third binding element; said fourth probe comprising a sequence that hybridizes to a fourth sequence in said second strand, said fourth sequence being between said polymorphic restriction site and the sequence in said second strand that is identical to the sequence of said second primer, and said fourth probe being immobilized on a fourth binding element.

44. The kit of claim 42, wherein said first and said second detectable labels are identical.

45. The kit of claim 42, wherein said first and second binding elements are each distinct regions on a solid support.

46. The kit of claim 45, wherein said solid support is glass.

47. The kit of claim 45, wherein said solid support is a microchip.

48. The kit of claim 43, wherein said one or more sets of said first, second, third, and fourth binding elements are each distinct regions on a solid support.

49. The kit of claim 48, wherein said solid support is glass.

50. The kit of claim 48, wherein said solid support is a microchip.

51. The method of claim 1, wherein said DNA is obtained from a plant.

52. The method of claim 1, wherein said DNA is obtained from a human.

53. The method of claim 1, wherein said DNA is obtained from a bacterium.

54. The method of claim 5, wherein said nucleic acid is obtained from a plant.

55. The method of claim 5, wherein said nucleic acid is obtained from a human.

56. The method of claim 5, wherein said nucleic acid is obtained from a bacterium.

57. The method of claim 13, wherein said nucleic acid is obtained from a plant.

58. The method of claim 13, wherein said nucleic acid is obtained from a human.

59. The method of claim 13, wherein said nucleic acid is obtained from a bacterium.

60. The method of claim 53, wherein said method is used for bacterial typing.

61. The method of claim 56, wherein said method is used for bacterial typing.

62. The method of claim 59, wherein said method is used for bacterial typing.

63. The method of claim 22, wherein said nucleic acid is obtained from a plant.

64. The method of claim 22, wherein said nucleic acid is obtained from a human.

65. The method of claim 22, wherein said nucleic acid is obtained from a bacterium.

66. The method of claim 65, wherein said method is used for bacterial typing.

* * * * *

UNITED STATES PATENT AND TRADEMARK OFFICE
CERTIFICATE OF CORRECTION

PATENT NO.  : 6,004,783
DATED       : December 21, 1999
INVENTORS   : Frederick M. Ausubel et al.

It is certified that error appears in the above-identified patent and that said Letters Patent is hereby corrected as shown below:

On the cover page, replace

"[75] Inventors: Frederick Ausubel, Newton, Mass.; Ronald W. Davis, Palo Alto; Daphne Preuss, Foster City, both of Calif."

with

"[75] Inventors: Frederick M. Ausubel, Newton; Stephen B. Calderwood, Wellesley, both of Mass."

Signed and Sealed this

Eleventh Day of April, 2000

Q. TODD DICKINSON

*Attest:*

*Attesting Officer*     *Director of Patents and Trademarks*